US012594261B2

(12) United States Patent
Chen et al.

(10) Patent No.: US 12,594,261 B2
(45) Date of Patent: Apr. 7, 2026

(54) USE OF HETEROCYCLIC DERIVATIVES WITH CARDIOMYOCYTE PROLIFERATION ACTIVITY FOR TREATMENT OF HEART DISEASES

(71) Applicant: SHANGHAI EAST HOSPITAL (EAST HOSPITAL, TONGJI UNIVERSITY SCHOOL OF MEDICINE), Shanghai (CN)

(72) Inventors: Yihan Chen, Shanghai (CN); Dandan Liang, Shanghai (CN); Yi Liu, Shanghai (CN); Subas Man Sakya, Shanghai (CN); Li Li, Shanghai (CN); Fulei Zhang, Shanghai (CN); Huixing Zhou, Shanghai (CN); Xiaoyu He, Shanghai (CN)

(73) Assignee: SHANGHAI EAST HOSPITAL (EAST HOSPITAL, TONGJI UNIVERSITY SCHOOL OF MEDICINE), Shanghai (CN)

( * ) Notice: Subject to any disclaimer, the term of this patent is extended or adjusted under 35 U.S.C. 154(b) by 902 days.

(21) Appl. No.: 17/755,399

(22) PCT Filed: Dec. 14, 2019

(86) PCT No.: PCT/CN2019/125455
§ 371 (c)(1),
(2) Date: Apr. 28, 2022

(87) PCT Pub. No.: WO2021/114315
PCT Pub. Date: Jun. 17, 2021

(65) Prior Publication Data

US 2022/0378748 A1 Dec. 1, 2022

(51) Int. Cl.
*A61K 31/4178* (2006.01)
*A61P 9/10* (2006.01)

(52) U.S. Cl.
CPC ............ *A61K 31/4178* (2013.01); *A61P 9/10* (2018.01)

(58) Field of Classification Search
CPC .............................. A61K 31/4178; A61P 9/10
See application file for complete search history.

(56) References Cited

FOREIGN PATENT DOCUMENTS

| | | | |
|---|---|---|---|
| CN | 103214422 | A | 7/2013 |
| WO | 2009050352 | A2 | 4/2009 |
| WO | 2014188193 | A1 | 11/2014 |
| WO | 2018081401 | A1 | 5/2018 |
| WO | 2019136320 | A1 | 7/2019 |

OTHER PUBLICATIONS

Debdad et al., J. Med. Chem. (2011) 54:4172-4186. (Year: 2011).*

Zhigang LI, et al., "GSK-3b inhibition protects the rat heart from the lipopolysaccharide-induced inflammation injury via suppressing FOXO3A activity," J Cell Mol Med., vol. 23, pp. 7796-7809, (2019).

Kouichi Hasegawa, et al., "Wnt Signaling Orchestration with a Small Molecule DYRK Inhibitor Provides Long-Term Xeno-Free Human Pluripotent Cell Expansion," Stem Cells Translational Medicine, vol. 1, pp. 18-28, (2012).

International Search Report issued Sep. 23, 2020 in PCT/CN2019/125455.

Written Opinion issued Sep. 23, 2020 in PCT/Cn2019/125455.

Debdab, M. et al, "Leucettines, a Class of Potent Inhibitors of cdc2-Like Kinases and Dual Specificity, Tyrosine Phosphorylation Regulated Kinases Derived from the Marine Sponge Leucettamine B: Modulation of Alternative Pre-RNA Splicing," J. Med. Chem., vol. 54, pp. 4172-4186, May 26, 2011.

Singh, A.P., et al., "Inhibition of GSK-3 to induce cardiomyocyte proliferation: a receipt for in situ cardiac regeneration," Cardiovascular Research, vol. 115, pp. 20-30, Oct. 15, 2018.

Li, Z., et al., "GSK-3b inhibition protects the rat heart from the lipopolysaccharide-induced inflammation injury via suppressing FOXO3A activity," J. Cell Mol. Med., vol. 23, No. 11, pp. 1-14, Sep. 10, 2019.

KHalifa, N.M., et al., "Synthesis of Some Novel 2-Thioxoimidazolidin-4-one Substituted Glycosyl Hydrazone Derivatives," Russian Journal of General Chemistry, vol. 87, No. 3, pp. 523-529, Dec. 31, 2017.

Porrello, Enzo R., et al., "Transient Regenerative Potential of the Neonatal Mouse Heart," Science, vol. 331, pp. 1078-1080, Feb. 25, 2011.

Zhu, Wuqiang, et al., "Regenerative Potential of Neonatal Porcine Hearts," Circulation, vol. 138, pp. 2809-2816, Dec. 11, 2018.

Schade, Dennis, et al., "Medicinal Chemistry Approaches to Heart Regeneration," J. Med. Chem. vol. 58, pp. 9451-9479, Aug. 19, 2015.

Fiedler, L.R., et al., MAP4K4 Inhibition Promotes Survical of Human Stem Cell-Derived Cardiomyocytes and REduces Infarct Size in Vivo, Cell Stem Cell, vol. 24, pp. 579-591, Apr. 4, 2019.

Loaëc, N., et al., "Marine-Derived 2-Aminoimidazolone Alkaloids, Leucettamine B-Related Polyandrocarpamines Inhibit Mammalian and Protozoan DYRK & CLK Kinases," Marine Drugs, vol. 15, 2017.

(Continued)

*Primary Examiner* — Marcos L Sznaidman
(74) *Attorney, Agent, or Firm* — Ice Miller LLP

(57) ABSTRACT

Provided herein is the use of heterocyclic derivatives with cardiomyocyte proliferation activity for treatment of heart diseases. Specifically, disclosed is the use of compounds of formula (I) or a pharmaceutically acceptable salt, a solvate, a stereoisomer or a prodrug thereof; and application thereof. Definition of each group in the formula can be found in the specification for details.

(I)

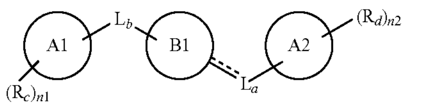

10 Claims, 3 Drawing Sheets

(56) References Cited

OTHER PUBLICATIONS

Saulnier, MG., et al., "An Efficient Method for the Synthesis of Guanidino Prodrugs," Bioorganic & Medicinal Chemistry Letters, vol. 4, No. 16, pp. 1985-1990, 1994.

Greenwald, Richard B., et al., "Drug Delivery Systems Based on Trimethyl Lock Lactonization: Poly(ethylene glycol) Prodrugs of Amino-Containing Compounds," J. Med. Chem. vol. 43, pp. 475-487, Jan. 19, 2000.

Roué, Nathalie, et al., "Synthesis of the Marine Alkaloid Leucettamine B," Tetrahedron, vol. 55, pp. 14729-14738, 1999.

Papeo, Gianluca, et al., "Discovery of 2-[1-(4,4-Difluorocyclohexyl)piperidin-4-yl]-6-fluoro-3-oxo-2,3-dihydro-1H-isoindole-4-carboxamide (NMS-P118): a Potent, Orally Available, and Highly Selective PARP-1 Inhibitor for Cancer Therapy," J. Med. Chem., vol. 58, pp. 6875-6989, Jul. 29, 20215.

Chen, Jinghai, et al., "mir-17-92 Cluster Is Required for and Sufficient to Induce Cardiomyocyte Proliferation in Postnatal and Adult Hearts," Circ Res 112, pp. 1557-1566 doi:10.1161/CIRCRESAHA.112.300658 (2013).

Andersson, Olov, et al., "Adenosine Signaling Promotes Regeneration of Pancreatic b Cells in Vivo," Cell Metabolism, vol. 15, pp. 885-894, Jun. 6, 2012.

Dogra, Deepika, et al., "Opposite effects of Activin type 2 receptor ligands on cardiomyocyte proliferation during development and repair," Nature Communications, vol. 8, No. 1902, (2017).

Hirose, Kentaro, et al., "Evidence for hormonal control of heart regenerative capacity during endothermy acquisition," Science, vol. 364, pp. 184-188, (2019).

Lin, Zhiqiang, et al., "Pi3kcb Links Hippo-YAP and PI3K-AKT Signaling Pathways to Promote Cardiomyocyte Proliferation and Survival," Circulation Research, vol. 116, pp. 35-45, doi:10.1161/CIRCRESAHA.115.304457 (2015).

Wang, Jinhu, et al., "Epicardial regeneration is guided by cardiac outflow tract and Hedgehog signalling," Nature, vol. 522, pp. 226-230, (2105).

Salic, Adrian, et al., "A chemical method for fast and sensitive detection of DNA synthesis in vivo," Proc. Natl. Acad. Science USA, vol. 105, No. 7, pp. 2415-2420, Feb. 19, 2008.

Wang, Qian, et al., "Bioconjugation by Copper(I)-Catalyzed Azide-Alkyne [3+ 2] Cycloaddition," J. Am. Chem. Soc, vol. 125, pp. 3192-3193, (2003).

Heallen, Todd, et al., "Hippo signaling impedes adult heart regeneration," Development, vol. 140, pp. 4683-4690 (2013).

* cited by examiner

Leucettamine B

Polyandrocarpamine A (R= Me)
Polyandrocarpamine B (R= H)

Phorbatopsin A

Dispacamide A 2-aminoimidazolin-4-one scaffold

Aplysinopsine

Hymenialdisine ($R_1$= H; $R_2$= Br)
Spongiacidin A ($R_1$= Br; $R_2$= Br)
Spongiacidin B ($R_1$= Br; $R_2$= H)

Clathridine (R= O)
Clathridimine (R= NH)

PAC1 PAC2 PAC3 PAC4 PAC5 PAC6 PAC7 PAC8 PAC9 PAC10 PAC11

USE OF HETEROCYCLIC DERIVATIVES WITH CARDIOMYOCYTE PROLIFERATION ACTIVITY FOR TREATMENT OF HEART DISEASES

CROSS-REFERENCE TO RELATED APPLICATION

This application is a Section 371 of International Application No. PCT/CN2019/125455, filed on Dec. 14, 2019, that published in the English language on Jun. 17, 2021, under International Publication No. WO 2021/114315 A1, the disclosure of which is incorporated herein by reference in its entirety.

FIELD OF INVENTION

The present invention belongs to the field of medical technology and pharmaceuticals, and specifically, relates to use of heterocyclic derivatives with cardiomyocyte proliferation activity for treatment of heart diseases.

BACKGROUND

Events leading to heart attack can be fatal. Most heart attack events are caused by cardiomyocyte death and thus loss of function of the heart muscles to pump blood which leads to asphyxiation of organs due to lack of oxygen. This can eventually lead to organ failures and potentially cause death. Prevention of heart attack normally means identifying the underlying disease early and try to intervene before heart attack takes place. In the event, that heart attack does take place, it is known that if one could grow back the cells and replace the dead cells in the heart, the heart attack would not be fatal. However, adult cardiomyocytes almost lose their ability to undergo cell division and proliferation after a narrow proliferative window at the neonatal stages (*Science* 2011; 331: 1078-1080; *Circulation* 2018; 24: 2809-2816). This terminal differentiation of the cardiomyocytes severely limits the repair of myocardial injury. Adult mammalian hearts form fibrotic scars in response to injury, which can lead to heart failure, arrhythmia and death. Current treatments can temporarily improve heart function but do not replace lost cardiomyocytes. Thus, multiple research areas have focused on agents that might regenerate heart cardiomyocytes via drug treatment or stem cell treatment.

Recent review article (J. Med. Chem. 2015, 58, 9451-9479) highlights many different approaches to treating heart disease related cardiomyocyte growth and proliferation. Number of kinase inhibitors, such as GSK b inhibitors are known to activate the WnT pathway leading to cell growth. Some of these compounds are also activators for stem cell differentiation. Another publication (Fiedler, L. R. et al. MAP4K4 Inhibition Promotes Survival of Human Stem Cell-Derived Cardiomyocytes and Reduces Infarct Size In Vivo. Cell Stem Cell 2019, 24, 579-591.e12) highlighted a MAP4K4 inhibitors that protect heart in acute myocardial infarction. Other kinase inhibitors, such as DYRK and CLK kinases inhibitors, are also known to help with cell growth as described in several other literature references especially pancreatic cell growth (WO 2018081401 and WO 2019136320). Others include CLK2 kinase inhibitors that have been shown to show growth of osteoclasts for osteoarthritis and have been shown to be useful for treatment of osteoarthritis.

It is an urgent need in the art to develop new medicine which can effectively and quickly promote cardiomyocyte proliferation or regeneration.

SUMMARY OF INVENTION

The object of the present invention is to provide novel compounds and medicines which can effectively and quickly promote cardiomyocyte proliferation or regeneration and treat heart attacks and heart infarction.

In the first aspect of the present invention, it provides a use of a compound of Formula I, or a pharmaceutically acceptable salt, a solvate, a stereoisomer or a prodrug thereof for manufacture of a medicament for treating or preventing a cardiovascular disease:

(I)

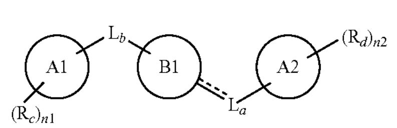

wherein each of ring A1 and ring A2 is independently selected from the group consisting of substituted or unsubstituted C3-C10 heterocyclic group, C4-C10 heteroaryl, C6-C10 aryl, wherein heterocycle and heteroaryl have 1-4 heteroatoms selected from N, O, S;

ring B is substituted 5-membered heteroaryl having two N heteroatoms or one N heteroatom and one S or O heteroatom, wherein 1 or 2 ring C atoms have an oxo (═O) substituent;

$- - -$ is a single or double bond;

La is absent, or a substituted or unsubstituted divalent or trivalent linkage group, and the number of skeleton linkage atom (N, C, O) is 1, 2 or 3, wherein La is a trivalent linkage group when $- - -$ is a double bond; and La is a divalent linkage group, when $- - -$ is a single bond;

Lb is a substituted or unsubstituted divalent linkage group, and the number of skeleton linkage atoms (N, C, O) is 1, 2 or 3;

$R_c$ and $R_d$ are independently selected from the group consisting of halogen (preferably, F, Cl, Br, I), —OH, nitro, cyano, sulfonyl, R", —N(R")$_2$—, R"—O—, R"—S—, R"—S(O)$_2$—, R"—S(O)—, R"—C(O), R"—C(O)O—, R"—OC(O)—; wherein R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl;

wherein two adjacent Rc may together form a substituted or unsubstituted C4-C8 heterocyclic ring, substituted or unsubstituted C4-C7 heteroaryl, substituted or unsubstituted C6 aryl;

wherein two adjacent Rd may together form a substituted or unsubstituted C4-C8 heterocyclic ring, substituted or unsubstituted C4-C7 heteroaryl, substituted or unsubstituted C6 aryl;

n1 and n2 are independently 0, 1, 2, 3, 4 or 5;

unless otherwise specified, the term "substituted" refers to one or more (preferably 1, 2, 3, 4 or 5) hydrogens in the group is replaced with an R' group;

each R' is independently selected from the group consisting of D, halogen (preferably F, Cl, Br, I), —OH, nitro, cyano, sulfonyl, R", —N(R"), R"—O—, R"—S—, R"—$S(O)_2$—, R"—S(O)—, R"—C(O), R"—C(O)O—, R"—OC(O)—, where R" is each independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, C1-C4 alkylene-C3-C6 cycloalkyl, —C1-C4 alkylene-C6-C10 aryl, —C1-C4 alkylene-(4 to 7-membered heterocycloalkyl), —C1-C4 alkylene-(5 to 7-membered heteroaryl);

and in R', the alkyl, alkenyl, alkynyl, cycloalkyl, aryl, heterocycloalkyl and heteroaryl, as a whole group or a partial group, can be optionally substituted by a substituent selected from the group consisting of: halogen (preferably F, Cl, Br, I), C1-C4 alkyl, C1-C4 alkoxy, C1-C4 haloalkyl, —OH, nitro, cyano, sulfonyl, and amino.

In another preferred embodiment, the cardiovascular disease is a heart disease.

In another preferred embodiment, the heart disease is selected from the group consisting of heart infarct, heart failure, atrial fibrillation, coronary heart disease, myocardial infarction, atrial septal defect, coronary artery disease, and combinations thereof.

In another preferred embodiment, in formula I, each of ring A1 and ring A2 is independently selected from the group consisting of substituted or unsubstituted C3-C10 heterocyclic group, C4-C10 heteroaryl, C6-C10 aryl, wherein heterocycle and heteroaryl have 1-4 heteroatoms selected from N, O, S;

ring B is substituted 5-membered heteroaryl having two N heteroatoms or one N heteroatom and one S or O heteroatom, wherein 1 or 2 ring C atoms have an oxo (═O) substituent;

╌╌ is a single or double bond;

La is absent, or a substituted or unsubstituted divalent or trivalent linkage group, and the number of skeleton linkage atom (N, C, O) is 1, 2 or 3, wherein La is a trivalent linkage group when ╌╌ is a double bond; and La is a divalent linkage group, when ╌╌ is a single bond;

Lb is a substituted or unsubstituted divalent linkage group, and the number of skeleton linkage atoms (N, C, O) is 1, 2 or 3;

$R_c$ and $R_d$ are independently selected from the group consisting of halogen (preferably, F, Cl, Br, I), —OH, nitro, cyano, sulfonyl, R", —$N(R")_2$—, R"—O—, R"—S—, R"—$S(O)_2$—, R"—S(O)—, R"—C(O), R"—C(O)O—, R"—OC(O)—; wherein R" is each independently selected from the group consisting of H, C1-C6 alkyl, C2-$C_6$ alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl;

wherein two adjacent Rc may together form a substituted or unsubstituted C4-C8 heterocyclic ring, substituted or unsubstituted C4-C7 heteroaryl, substituted or unsubstituted C6 aryl;

wherein two adjacent Rd may together form a substituted or unsubstituted C4-C8 heterocyclic ring, substituted or unsubstituted C4-C7 heteroaryl, substituted or unsubstituted C6 aryl;

n1 and n2 are independently 0, 1, 2, 3, 4 or 5;

unless otherwise specified, the term "substituted" refers to one or more (preferably 1, 2, 3, 4 or 5) hydrogens in the group is replaced with an R' group;

each R' is independently selected from the group consisting of D, halogen (preferably F, Cl, Br, I), —OH, nitro, cyano, sulfonyl, R", —N(R"), R"—O—, R"—S—, R"—$S(O)_2$—, R"—S(O)—, R"—C(O), R"—C(O)O—, R"—OC(O)—, where R" is each independently selected from the group consisting of H, C1-C6 alkyl, C2-C6 alkenyl, C2-$C_6$ alkynyl, C3-C8 cycloalkyl, C6-C10 aryl, 4- to 7-membered heterocycloalkyl, 5- to 7-membered heteroaryl, C1-C4 alkylene-C3-C6 cycloalkyl, —C1-C4 alkylene-C6-C10 aryl, —C1-C4 alkylene-(4 to 7-membered heterocycloalkyl), —C1-C4 alkylene-(5 to 7-membered heteroaryl);

and in R', the alkyl, alkenyl, alkynyl, cycloalkyl, aryl, heterocycloalkyl and heteroaryl, as a whole group or a partial group, can be optionally substituted by a substituent selected from the group consisting of: halogen (preferably F, Cl, Br, I), C1-C4 alkyl, C1-C4 alkoxy, C1-C4 haloalkyl, —OH, nitro, cyano, sulfonyl, and amino;

with the proviso that:

(A) when Lb, ring B and La together form

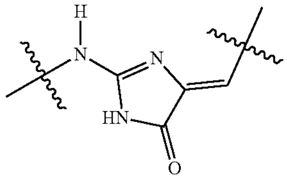, then (P1) ring A1 is not a substituted or unsubstituted phenyl; or (P2) ring A2 is not selected from the group consisting of:

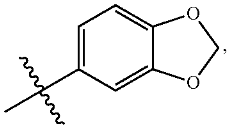, 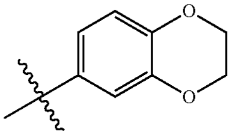,

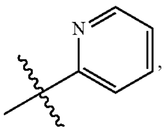, 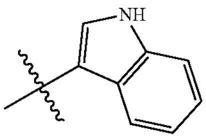,

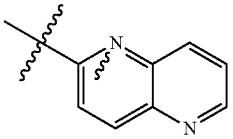

and substituted or unsubstituted phenyl; or, (P3) ring A1 and/or ring A2 is selected from the group consisting of:

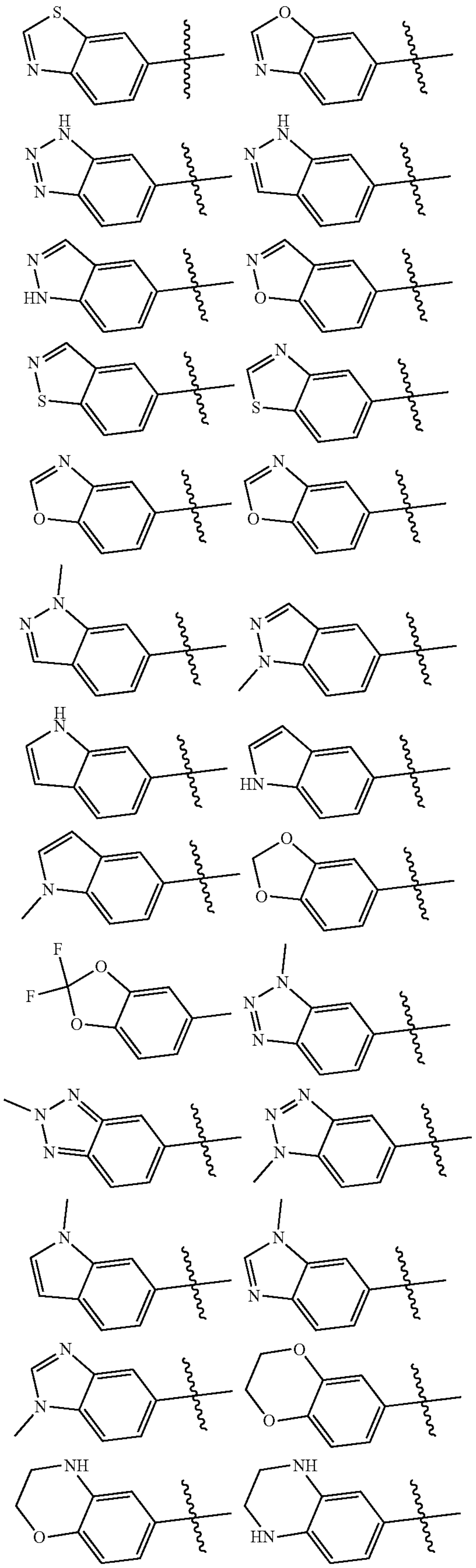
-continued
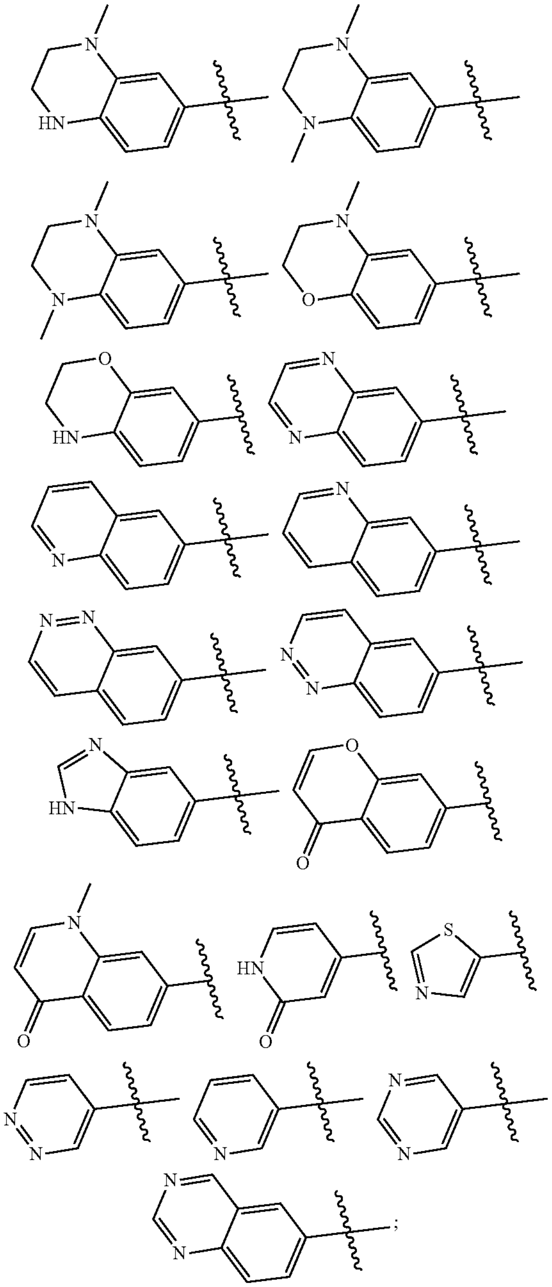
;
or
(B) both ring A1 and ring A2 are not a substituted or unsubstituted phenyl; or
(C) ring A2 is not
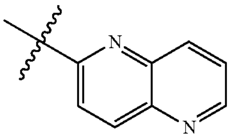
.
In another preferred example, wherein the compound of Formula I has a structure of Formula (B)

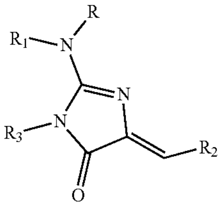

General Formula (B)

wherein,

R=Alkyl, Aryl, $SO_2$Alkyl, or COAlkyl;

R1=Alkyl, Aryl, or Heteroaryl;

R3=alkyl, aryl, heteroaryl, etc;

R2=heteroaryl.

In another preferred example, the compound is selected from Table B.

TABLE B

| Compound ID | Name |
|---|---|
| TJU-B001 | (4Z)-2-amino-1-methyl-4-[(naphthalen-2-yl)methylidene]-4,5-dihydro-1H-imidazol-5-one |
| TJU-B003 | (4Z)-2-amino-4-[(4-chlorophenyl)methylidene]-1-methyl-4,5-dihydro-1H-imidazol-5-one |
| TJU-B004 | (4Z)-4-[(2H-1,3-benzodioxol-5-yl)methylidene]-2-{[2-(morpholin-4-yl)ethyl] amino}-4,5-dihydro-1H-imidazol-5-one |
| TJU-B005 | 4-[(2H-1,3-benzodioxol-5-yl)methyl]-2-(phenylamino)-4,5-dihydro-1H-imidazol-5-one |
| TJU-B006 | (4Z)-4-[(2,3-dihydro-1,4-benzodioxin-6-yl)methylidene]-2-[(4-methoxyphenyl) amino}-4,5-dihydro-1H-imidazol-5-one |
| TJU-B007 | (4Z)-4-[(2,3-dihydro-1,4-benzodioxin-6-yl)methylidene]-2-(phenylamino)-4,5-dihydro-1H-imidazol-5-one |
| TJU-B009 | (4Z)-4-[(2H-1,3-benzodioxol-5-yl)methylidene]-2-[(4-methoxyphenyl)amino]-4,5-dihydro-1H-imidazol-5-one |
| TJU-B011 | (4Z)-4-[(6-chloro-2H-1,3-benzodioxol-5-yl)methylidene]-2-(phenylamino)-4,5-dihydro-1H-imidazol-5-one |
| TJU-B013 | (4Z)-4-[1-(2H-1,3-benzodioxol-5-yl)ethylidene]-2-(phenylamino)-4,5-dihydro-1H-imidazol-5-one |
| TJU-B014 | (4Z)-4-[(2H-1,3-benzodioxol-5-yl)methylidene]-1-methyl-2-(phenylamino)-4,5-dihydro-1H-imidazol-5-one |
| TJU-B016 | (4Z)-4-[(2H-1,3-benzodioxol-5-yl)methylidene]-1-methyl-2-[(propan-2-yl)amino]-4,5-dihydro-1H-imidazol-5-one |
| TJU-B019 | (4Z)-4-[(2H-1,3-benzodioxol-5-yl)methylidene]-2-(benzylamino)-4,5-dihydro-1H-imidazol-5-one |
| TJU-B021 | (4Z)-2-[(4-aminophenyl)amino]-4-[(2H-1,3-benzodioxol-5-yl)methylidene]-4,5-dihydro-1H-imidazol-5-one |
| TJU-B026 | (4Z)-4-[(2,3-dihydro-1,4-benzodioxin-6-yl)methylidene]-2-{[2-(morpholin-4-yl)ethyl] amino}-4,5-dihydro-1H-imidazol-5-one |
| TJU-B027 | (4Z)-2-[(2H-1,3-benzodioxol-5-yl)amino]-4-[(2H-1,3-benzodioxol-5-yl)methylidene]-4,5-dihydro-1H-imidazol-5-one |
| TJU-B028 | (4Z)-4-[(2,2-difluoro-2H-1,3-benzodioxol-5-yl)methylidene]-2-(phenylamino)-4,5-dihydro-1H-imidazol-5-one |
| TJU-B029 | (4Z)-4-[(2H-1,3-benzodioxol-5-yl)methylidene]-2-[(cyclopropylmethyl)amino]-4,5-dihydro-1H-imidazol-5-one |
| TJU-B031 | (4Z)-4-[(2H-1,3-benzodioxol-5-yl)methylidene]-2-[(pyridin-3-yl)amino]-4,5-dihydro-1H-imidazol-5-one |
| TJU-B033 | (4Z)-4-[(2H-1,3-benzodioxol-5-yl)methylidene]-2-(methylamino)-4,5-dihydro-1H-imidazol-5-one |
| TJU-B034 | (4Z)-2-amino-4-[(2H-1,3-benzodioxol-5-yl)methylidene]-4,5-dihydro-1H-imidazol-5-one |
| TJU-B036 | (4Z)-2-amino-4-[(3-methoxyphenyl)methylidene]-1-methyl-4,5-dihydro-1H-imidazol-5-one |
| TJU-B038 | (4Z)-4-[(2H-1,3-benzodioxol-5-yl)methylidene]-2-[(propan-2-yl)amino]-4,5-dihydro-1H-imidazol-5-one |
| TJU-B039 | (4Z)-4-[(2H-1,3-benzodioxol-5-yl)methylidene]-2-phenyl-4,5-dihydro-1H-imidazol-5-one |
| TJU-B040 | (4Z)-4-[(2H-1,3-benzodioxol-5-yl)methylidene]-2-(ethylamino)-4,5-dihydro-1H-imidazol-5-one |
| TJU-B043 | (4Z)-4-[(2H-1,3-benzodioxol-5-yl)methylidene]-2-(phenylamino)-4,5-dihydro-1H-imidazol-5-one |
| TJU-B045 | (4Z)-2-amino-1-methyl-4-(phenylmethylidene)-4,5-dihydro-1H-imidazol-5-one |
| TJU-B049 | (4Z)-2-amino-4-[(2,2-difluoro-2H-1,3-benzodioxol-5-yl)methylidene]-4,5-dihydro-1H-imidazol-5-one |
| TJU-B050 | (4Z)-2-amino-4-[(4-fluorophenyl)methylidene]-1-methyl-4,5-dihydro-1H-imidazol-5-one |
| TJU-B051 | (4Z)-4-[(7-methoxy-2H-1,3-benzodioxol-5-yl)methylidene]-2-(phenylamino)-4,5-dihydro-1H-imidazo 1-5-one |
| TJU-B052 | (4Z)-4-[(2H-1,3-benzodioxol-5-yl)methylidene]-2-[(cyclopropylmethyl)amino]-1-methyl-4,5-dihydro-1H-imidazol-5-one |
| TJU-B056 | (4Z)-2-amino-4-[(3-chlorophenyl)methylidene]-1-methyl-4,5-dihydro-1H-imidazol-5-one |

TABLE B-continued

| Compound ID | Name |
|---|---|
| TJU-B057 | (4Z)-2-amino-4-[(2H-1,3-benzodioxol-5-yl)methylidene]-1-methyl-4,5-dihydro-1H-imidazol-5-one |
| TJU-B058 | 4-{[(4Z)-4-[(2H-1,3-benzodioxol-5-yl)methylidene]-5-oxo-4,5-dihydro-1H-imidazol-2-yl] amino {benzonitrile |
| TJU-B059 | (4Z)-4-[(2H-1,3-benzodioxol-5-yl)methylidene]-2-cyclopropyl-4,5-dihydro-1H-imidazol-5-one |
| TJU-B060 | (4Z)-4-[(2H-1,3-benzodioxol-5-yl)methylidene]-2-[(4-chlorophenyl)amino]-4,5-dihydro-1H-imidazo 1-5-one |
| TJU-B063 | (4Z)-4-[(2,2-difluoro-2H-1,3-benzodioxol-5-yl)methylidene]-2-phenyl-4,5-dihydro-1H-imidazol-5-one |
| TJU-B064 | (4Z)-2-amino-4-[(6-chloro-2H-1,3-benzodioxol-5-yl)methylidene]-4,5-dihydro-1H-imidazol-5-one |
| TJU-B065 | (4Z)-2-amino-4-[(7-methoxy-2H-1,3-benzodioxol-5-yl)methylidene]-4,5-dihydro-1H-imidazol-5-one |
| TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| TJU-B067 | (4Z)-2-amino-4-[(2-fluorophenyl)methylidene]-1-methyl-4,5-dihydro-1H-imidazol-5-one |
| TJU-B070 | (4Z)-2-amino-4-[(3,4-dimethoxyphenyl)methylidene]-1-methyl-4,5-dihydro-1H-imidazol-5-one |
| TJU-B085 | (4Z)-4-[(3,4-dimethoxyphenyl)methylidene]-2-(phenylamino)-4,5-dihydro-1H-imidazol-5-one |
| TJU-B088 | (4Z)-2-[(2H-1,3-benzodioxol-5-yl)amino]-4-[(2H-1,3-benzodioxol-5-yl) methylidenel-1-methyl-4,5-dihydro-1H-imidazol-5-one |
| TJU-B097 | (4Z)-4-[(2H-1,3-benzodioxol-5-yl)methylidene]-2-[(pyridin-2-yl)amino]-4,5-dihydro-1H-imidazol-5-one |
| TJU-B110 | (4Z)-4-[(2H-1,3-benzodioxol-5-yl)methylidene]-2-[(4-methylphenyl)amino]-4,5-dihydro-1H-imidazo 1-5-one |
| TJU-B253 | (4Z)-4-[(2H-1,3-benzodioxol-5-yl)methylidene]-2-(cyclohexylamino)-4,5-dihydro-1H-imidazol-5-one |
| TJU-B254 | (4Z)-4-[(2H-1,3-benzodioxol-5-yl)methylidene]-2-[(2-methoxyphenyl)amino]-4,5-dihydro-1H-imidazol-5-one |

In another preferred example, the compound is L41, a pharmaceutically acceptable salt, a solvate, a stereoisomer or a prodrug, or a derivative compound thereof:

L41

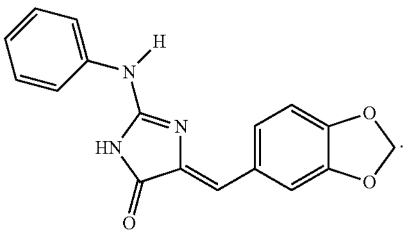

In the second aspect of the present invention, it provides a method for promoting growth of cardiomyocytes in vitro, which comprises a step of:

culturing cardiomyocyte in the present of a compound of Formula I, or a pharmaceutically acceptable salt, a solvate, a stereoisomer or a prodrug.

In the third aspect of the present invention, it provides a method for promoting cardiomyocyte proliferation and/or regeneration of cardiomyocyte in vitro, which comprises a step of:

contacting cardiomyocyte with a compound of Formula I, or a pharmaceutically acceptable salt, a solvate, a stereoisomer or a prodrug, thereby promoting cardiomyocyte proliferation and/or regeneration.

In the fourth aspect of the present invention, it provides a method for treating a cardiovascular disease, which comprises a step of: administering a compound of Formula I or a pharmaceutically acceptable salt, a solvate, a stereoisomer or a prodrug to a subject in need.

In another preferred embodiment, the subjects comprises human and non-human mammal.

In the fifth aspect of the present invention, it provides a pharmaceutical composition for treating heart disease, which comprises the compound of formula I, or a pharmaceutically acceptable salt, solvate, stereoisomer, or prodrug thereof, and a pharmaceutically acceptable carrier.

In another preferred embodiment, the pharmaceutical composition is used to promote cardiomyocyte proliferation and/or regeneration It should be understood that each of the above technical features of the invention and each technical feature specifically described below (such as in Examples) can be combined with each other within the scope of the present invention so as to constitute new or preferred technical solutions.

DETAILED DESCRIPTION OF INVENTION

Figure 1:
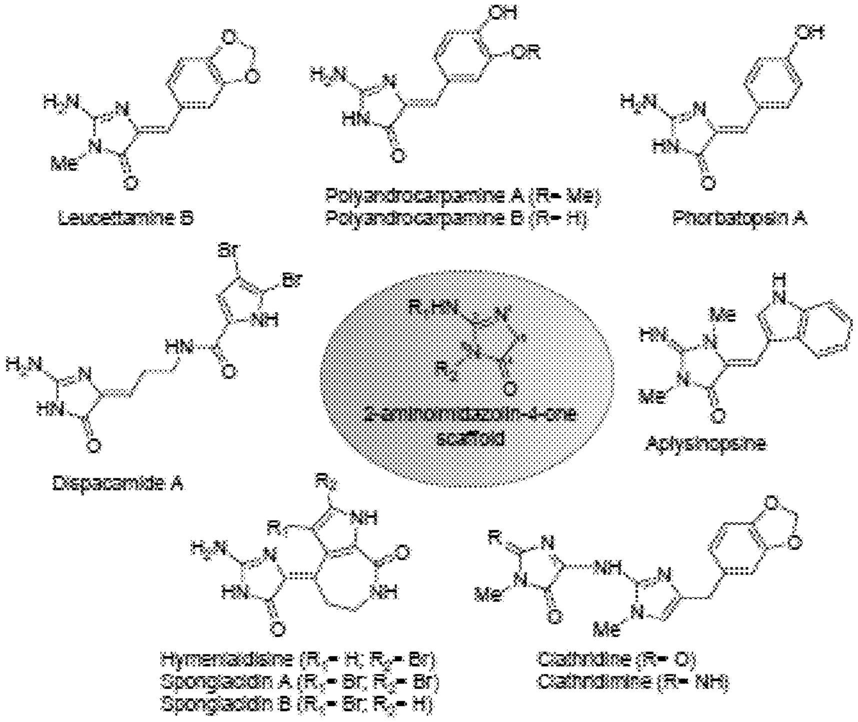
FIG. 1 and FIG. 2 show several analogs of marine natural products related to Leucettines disclosed by Marine Drugs 2017, 15, 316.

After extensive and intensive research, the inventors have expectantly found that compounds of formula I have the ability promoting cardiomyocyte growth. During heart attacks, cardiomyocyte death usually leads to irrecoverable damage to the heart leading to eventual death. The biological assay demonstrates that compounds of formula (I) can effectively stimulate proliferation and regeneration of cardiomyocytes. The present invention is completed on this basis.

Definition of Terms

As used herein, term “C1-6 alkyl” refers to a straight or branched saturated aliphatic hydrocarbon group having 1 to 6 carbon atoms, for example, methyl, ethyl, propyl, isopropyl, n-butyl, iso-butyl, tert-butyl, pentyl, hexyl and the like, and preferably alkyl having 1 to 4 carbon atoms, and more preferably alkyl having 1 to 3 carbon atoms.

As used herein, term “C2-6 alkenyl” refers to a straight or branched unsaturated aliphatic hydrocarbon group having 2 to 6 (preferably 2 to 4) carbon atoms and carbon-carbon double bond (C═C), for example ethenyl, propenyl, isopropenyl, n-butenyl, iso-butenyl, pentenyl, hexenyl and the like.

As used herein, term “C2-6 alkynyl” refers to a straight or branched unsaturated aliphatic hydrocarbon group having 2 to 6 (preferably 2 to 4) carbon atoms and carbon-carbon triple bond, for example ethynyl, propynyl, n-butynyl, isobutynyl, pentynyl, hexynyl and the like.

As used herein, term “C3-8 cycloalkyl” refers to cycloalkyl having 3 to 8 carbon atoms, for example cyclopropyl, cyclobutyl, cyclopentyl, cyclohexyl and the like.

As used herein, term “C1-4 alkoxy” refers to C1-4 alkyl-O—, for example methoxy, ethoxy, propoxy, butoxy and the like.

As used herein, term “C6-10 aryl” refers to aromatic hydrocarbon group having 6 to 10 carbon atoms, for example phenyl, naphthyl and the like. As used herein, term “halogen” refers to fluorine, chlorine, bromine or iodine.

As used herein, term “divalent C1-4 hydrocarbyl” refers to a straight or branched alkylidene(or “alkylene group”), alkenylidene or alkynylidene, wherein, “alkylidene” or “alkylene group” refers to divalent alkyl, for example, methylidene, ethylidene and the like; and “alkenylidene” refers to divalent alkenyl. “Alkylidene is replaced” refers to the methylidene in the divalent straight or branched $C_{1-3}$ hydrocarbyl may be replaced with the groups as defined herein, for example, it is $—CH_2—S(O)—CH_2—$, $—CH_2—O—CH_2—$, $—CH_2—C(O)NR^y—CH_2—$, $—C(O)—CH_2—CH_2—$, $—CH_2—C(R^yR^x)—CH_2—$, $—N(R^y)—CH_2—CH_2—$, $—C(R^yR^x)—C(R^yR^x)—CH_2—$ and the like after replacement.

Unless specifically defined, the term “cycloalkyl” is also meant to refer to bicyclic and polycyclic hydrocarbon rings such as, for example, bicyclo[2.2.1]heptane, bicyclo[2.2.2]octane, etc.

Unless specifically defined, the term “heterocycloalkyl” refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

Unless specifically defined, the term “aryl” means, unless otherwise stated, a polyunsaturated, typically aromatic, hydrocarbon group which can be a single ring or multiple rings (up to three rings) which are fused together or linked covalently.

Unless specifically defined, the term “heteroaryl” refers to aryl groups (or rings) that contain from one to five heteroatoms selected from N, O, and S, wherein the nitrogen and sulfur atoms are optionally oxidized, and the nitrogen atom (s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzooxazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, pyrrolopyridyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

Active Ingredient

In the present invention, it provides an new active ingredient for promoting cardiomyocyte proliferation which has a general formula (I) as defined in the first aspect of invention.

Preferably, the active compound is one listed in Tables B, or a pharmaceutically acceptable salt, a solvate, a stereoisomer or a prodrug thereof.

Preferably, one class of compounds are analogs of imidazolone class of compounds which are analogs of L41.

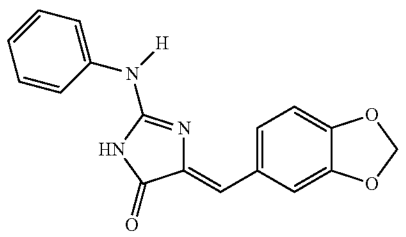

L41

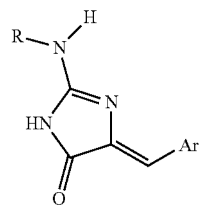

L41G

-continued

L41A1

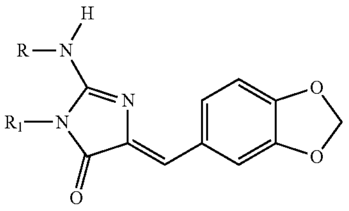

L41A2

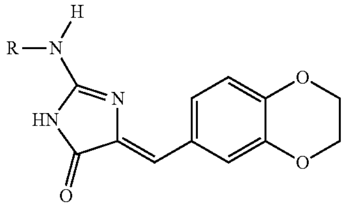

wherein in formula L41G, L41A1 and L41A2

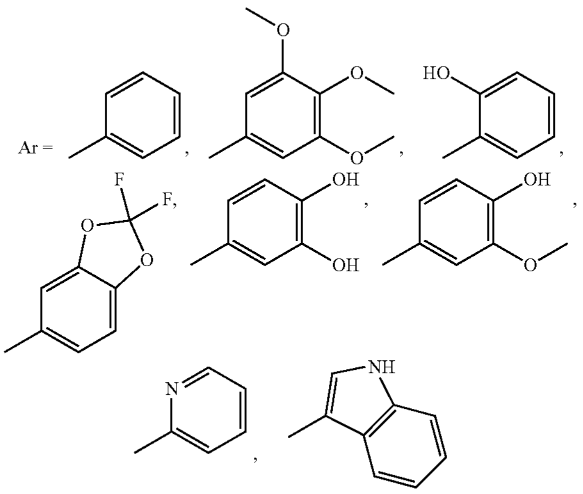

R=H, alkyl, amide and substituted aryl groups.

Figure 2:
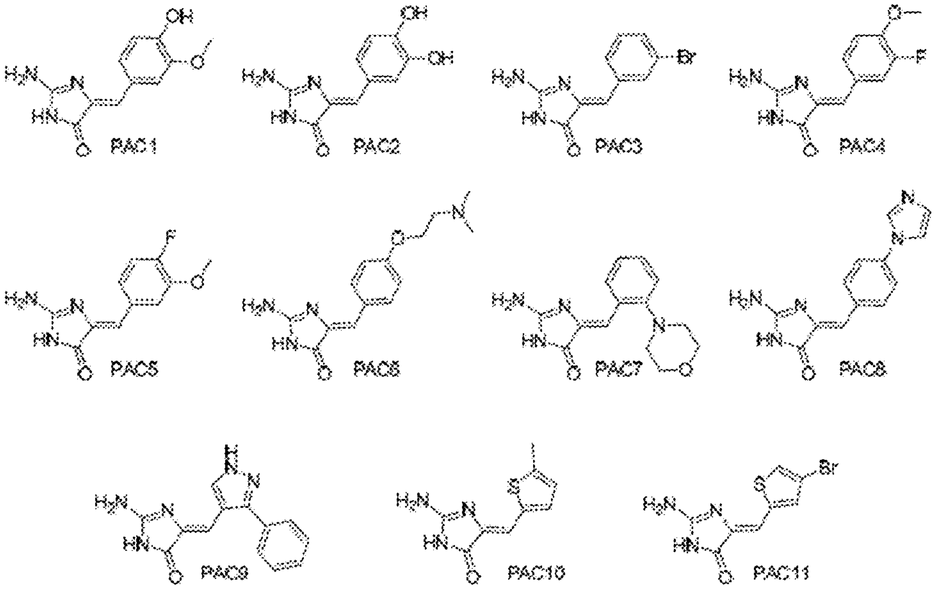

Another class of analogs useful in the present invention are shown in the FIGS. 1 and 2.

Another class of analogs useful in the present invention are shown as follows:

I

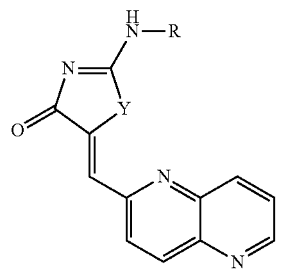

wherein R1=Aryl and heteroaryl groups.

Pharmaceutical Composition

Generally, the compound of the present invention or a pharmaceutically acceptable salt solvate, stereoisomer, or prodrug thereof may form a suitable dosage form for administration with one or more pharmaceutically acceptable carriers. These dosage forms are suitable for oral, rectal, topical, intraoral administration, and other parenteral administration (e.g., subcutaneous, intramuscular, intravenous administration, etc.). For example, dosage forms suitable for oral administration include capsules, tablets, granules and syrups. Compounds of the present invention contained in these formulations may be solid powders or granules; solutions or suspensions in aqueous or non-aqueous liquid; water-in-oil or oil-in-water emulsions etc. Such dosage forms may be prepared with active compounds and one or more carriers or excipients through the conventional pharmacy methods. The above-mentioned carriers should be compatible with active compounds or other excipients. For solid formulations, conventional non-toxic carriers include, but not limited to mannitol, lactose, starch, magnesium stearate, cellulose, glucose, sucrose and the like. Carriers used for liquid preparations include water, saline, aqueous dextrose, ethylidene glycol, polyethylidene glycol and the like. The active compounds may form a solution or suspension with the above-mentioned carriers.

The compositions of the present invention are formulated, quantified and administrated in a manner consistent with the practice of medicine. The "effective amount" of the administrated compound depends on the factors such as the specific disease to be treated, the individual being treated, the cause of diseases, the drug targets and the mode of administration, etc.

As used herein, term "pharmaceutically acceptable salt (s)" includes pharmaceutically acceptable acid addition salt (s) and base addition salt(s).

As used herein, term "pharmaceutically acceptable acid addition salts" refer to salts that are able to retain the biological effectiveness of the free base without other side effects and are formed with inorganic or organic acids. Inorganic acid salts include, but not limited to, hydrochloride, hydrobromide, sulfate, phosphate and the like; organic acid salts include, but not limited to, formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art.

"Pharmaceutically acceptable base addition salts" include, but not limited to the salts of inorganic bases such as sodium, potassium, calcium and magnesium salts, and include but not limited to the salts of organic bases, such as ammonium salt, triethylamine salt, lysine salt, arginine salt and the like. These salts can be prepared by the methods known in the art.

As used herein, the compounds of formula (I) may exit in one or more crystalline forms. The active compounds of the present invention include various polymorphs and mixtures thereof.

The "solvate" mentioned in the present invention refers to a complex formed with the compound of the present invention and a solvent. The solvate can be formed either through a reaction in a solvent or precipitated or crystallized from the solvent. For example, a complex formed with water is referred to as "hydrate". The solvates of the compounds of formula (I) are within the scope of the present invention.

The compounds of formula (I) of the invention may contain one or more chiral centers, and may exist in different optically active forms. When the compound contains one chiral center, the compound includes enantiomers. The present invention includes both of two isomers and a mixture thereof, such as racemic mixtures. Enantiomers can be resolved using methods known in the art, such as crystallization and chiral chromatography and the like. When the compound of formula (I) contain more than one chiral centers, the compounds may include diastereomers. The present invention includes specific isomers resolved into optically pure isomers as well as the mixtures of diastereomeric isomers. Diastereomeric isomers can be resolved using methods known in the art, such as crystallization and preparative chromatography.

The present invention includes prodrugs of the above-mentioned compounds. Prodrugs include known amino protecting groups and carboxyl protecting groups which are hydrolyzed under physiologic conditions or released by enzyme reaction to obtain the parent compounds. Specific preparation methods of prodrugs can refer to (Saulnier, M G; Frennesson, D B; Deshpande, M S; Hansel, S B and Vysa, D M Bioorg. Med. Chem Lett. 1994, 4, 1985-1990; and Greenwald, R B; Choe, Y H; Conover, C D; Shum, K.; Wu, D.; Royzen, M. J. Med. Chem. 2000, 43, 475).

As used herein, term "therapeutically effective amount" refers to an amount that yields a function or activity to humans and/or animals and may be tolerated by humans and/or animals.

The pharmaceutical composition provided by the present invention preferably contains the active ingredient in a weight ratio of 1 to 99%. Preferably, the compound of the general formula I accounts for 65 wt % to 99 wt % of the total weight as the active ingredient, and the rest are pharmaceutically acceptable carriers, diluents, solutions or salt solutions.

The compounds and pharmaceutical compositions provided by the present invention may be in various forms, such as tablets, capsules, powders, syrups, solutions, suspensions, aerosols, etc., and may be present in suitable solid or liquid carriers or diluents, and in disinfectors suitable for injection or instillation.

field. The unit dosage of its formulation formula comprises 0.05-200 mg of the compound of formula I, preferably, the unit dosage of the formulation formula contains 0.1 mg-100 mg of the compound of formula I.

The compounds of the present invention may be administered alone or in combination with other pharmaceutically acceptable compounds (such as other drugs for treating heart diseases).

The compounds and pharmaceutical compositions of the present invention can be used clinically in mammals, including humans and animals, and can be administered via mouth, nose, skin, lung or gastrointestinal tract. Most preferred is oral. The most preferred daily dose is 0.01-200 mg/kg body weight in one dose, or 0.01-100 mg/kg body weight in divided doses. Regardless of the administering method, the individual's optimal dose should be based on the specific treatment. Usually, it starts with a small dose, which is gradually increased until the most suitable dose is found.

Preparation Method

The present invention provides preparation methods of compounds of formula (I). The compounds of the present invention can be easily prepared by a variety of synthetic operations, and these operations are familiar to those skilled in the art. An exemplary preparation of these compounds may include (but not limited to) the processes described below.

Generally, in the preparation process, each reaction is generally conducted in an inert solvent, under room temperature to reflux temperature (such as 0-150° C., preferably from 0-100° C.). The reaction time is usually 0.1 hours-60 hours, preferably 0.5 to 48 hours.

Preferably, Compounds of formula (I) of the present invention can be prepared referring to the following schemes. The procedures of method can be extended or combined as desired in practice.

Scheme 1

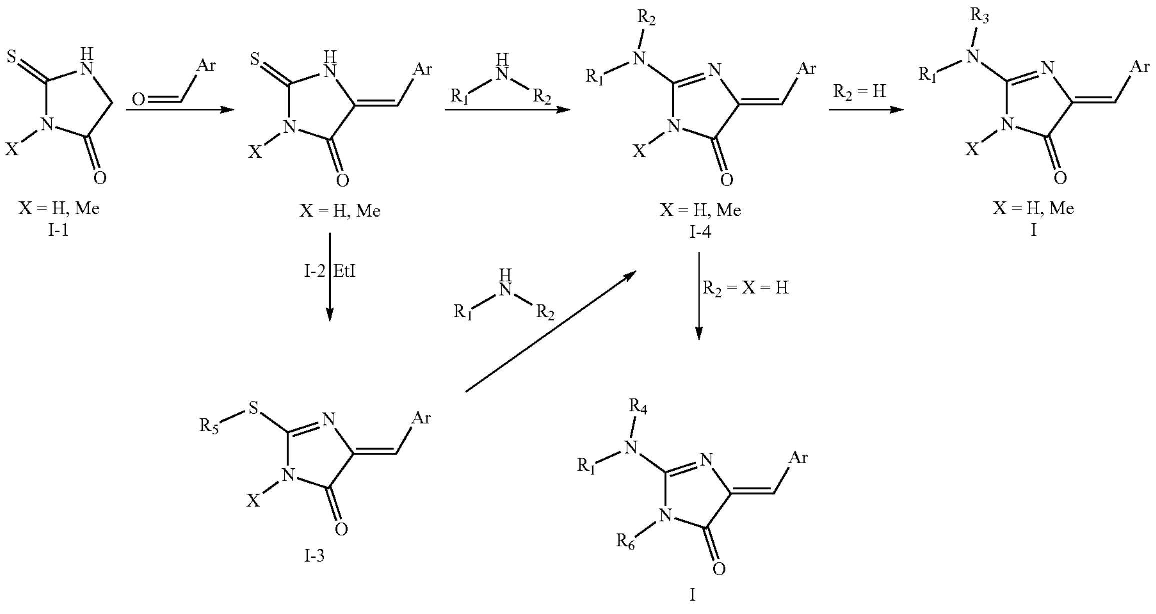

Various dosage forms of the pharmaceutical compositions of the present invention can be prepared according to the conventional preparation methods in the pharmaceutical Scheme shows one route that can be used to access most of the targets synthesized in this patent. Intermediate I-1 can be made using route described in Rou e, N.; Bergman, J.

Synthesis of the marine alkaloid leucettamine B. Tetrahedron 1999, 55, 14729-14738 and J. Med. Chem. 2011, 54, 4172-4186. Compounds of formula I-1 are available commercially or prepared through methods known to the skilled in the art based on literature reported conditions (J. Med. Chem 2015, 58(17), 6889; WO2014188193, 2014) The reagent aldehyde and amines used to make the targets are also commercially available or can be prepared through methods known to those skilled in the art.

Compound I-1 can be prepared by the following reaction.

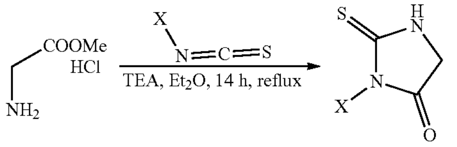

Reaction of I-1 with aldehyde using catalytic base such as Et3N, DIPEA, piperidine, etc in alcoholic or aprotic solvent will provide intermediate I-2. This intermediate then can be reacted in the presence of an oxidang such as TBHP and amines, either primary or secondary amines, to give the desired targets I-4. Detailed conditions mentioned have been described in the J. Med, Chem. 2011, 54, 4172-486. In the case of primary amines (R2=H), the product I-4 can be treated with acid chlorides, sulfonyl chlorides and alkyl halides in the presence of base such as NaH, $K_2CO_3$, $Et_3N$, DIPEA, etc to give the amide, sulfonamide or di-alkyl amino targets I where $R_3$ is $COR_7$, $SO_2R7$ or alkyl groups.

I-2 can also be alkylated with R3X where R3 is alkyl and X is halide or O-sulfones to give I-3. This can then be reacted with primary or secondary amines in the presence of base (alkyl amines or inorganic base) to give I-4. This can further be reacted with R6X to give alkylated targets I where $R_4$ is also alkyl. If $R_2$ is H, then both $R_4$ and $R_6$ can be the same after alkylation with $R^6X$.

Compounds of formula (I), preparation methods thereof, pharmaceutical compositions and treatment protocols disclosed in the present invention can be achieved by the person skilled in the art through appropriate improvements of process parameters referring to this disclosure of invention. It should be particularly noted that all such alterations and changes are obvious to the skilled artisan, and they are deemed to be included in the present invention. Preferred embodiments of products, methods and applications of the present invention have been described, and relevant personnel can obviously alter or change and combine the methods and uses of the present invention without departing from the content, spirit and scope of the present invention for implementation and application of the present technology.

The main advantages of the present invention include:

(1) The compounds of the present invention show a high inhibitory activity against CLK1 (such as CLK1A) and DYRK1.

(2) The compounds of the present invention exhibit selectivity against GSKb.

(3) Most importantly, the compounds of the present invention exhibit superior myocyte proliferation activity, and therefore are useful for treating heart diseases relating to cardiomyocyte.

(4) The compounds of formula I and especially L41 and its analogs have potent activity in vitro assay as measured with DNA proliferation assay using EDU as endpoint. Further, the in vivo experiment in the heart infarct model also has confirmed that the compound of the invention (especially L41 and its analogs) have superior cardiomyocyte proliferation activity for treatment of heart diseases.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless defined otherwise, terms used herein are the same as those familiar to the skilled in the art. Moreover, any method or material similar or equivalent to those recorded in the present invention can be used in the present invention.

Reagents and Instruments

All reactions were conducted under an atmosphere of dry nitrogen unless specified otherwise. Reactions were monitored with TLC plates, which were visualized with u.v. light or appropriate stains. Flash chromatography refers to column chromatography over silica gel (40-60 μm) using glass columns. Alternatively, automated chromatography was performed using ISCO, Biotage SP1 or Biotage Isolera systems with u.v. detection at 220 or 254 nm and employing Biotage normal phase or reverse phase silica cartridges. Further details can be found under the relevant experimental procedure.

The following system was used for LCMS: Agilent 6120 (binary pump), Waters CORTECS column C18, 2.7 μm, 4.6×30 mm, 45° C., 1 μL injection volume, 1.8 mL/min, with a gradient of acetonitrile in 0.05% aqueous formic acid according to the following timings:

| Time(min) | Acetonitrile (0.05% FA) (%) | $H_2O$ (0.05% FA) (%) |
|---|---|---|
| 0.00 | 5 | 95 |
| 0.80 | 95 | 5 |
| 1.60 | 95 | 5 |
| 1.61 | 5 | 95 |
| 2.00 | 5 | 95 |

The following systems were used for UPLC (no mass spectrometry): Waters H-Class (quaternary pump), Waters ACQUITY BEH C18 1.7 μm, 2.1×50 mm, 0.5 mL/min, 45° C.; gradient 5-95% acetonitrile in 0.05% aqueous trifluoroacetic acid over 2 min, then hold 95% acetonitrile 0.5 min re-equilibrate back to 5% Acetonitrile to 2.7 min, Total 3.5 min. NMR spectra were measured with a Bruker spectrometer operating at 400 MHz (1H), 376 MHz (19F) or 100 MHz (13C). Solvents used for samples are specified in the experimental procedures for each compound.

$^1$HNMR: Bruker AVANCE-400 NMR machine. The internal standard was tetramethylsilane (TMS).

Preparative high performance liquid chromatography (pre-HPLC): Waters PHW007, column XBridge C18, 4.6×150 mm, 3 Sum.

Using ISCO Combiflash-Rf75 or Rf200 automatic eluting column instrument, Agela 4 g, 12 g, 20 g, 40 g, 80 g, 120 g disposable silica gel column.

The known starting materials of the invention are synthesized by the methods known in the art, or are purchased from Bide Chemical ltd., Bridge, Combi Blocks, Wuxi Lab Networks, Acros Organics, Aldrich Chemical Company, Accela ChemBio Inc and Darui Chemical Company etc.

All examples were performed under nitrogen or argon atmosphere and the solution refers to aqueous solution if without special explanation.

In the examples, the reaction process was monitored by thin layer chromatography (TLC), compounds were purified by column chromatography. The eluent used in Column chromatography or TLC were selected from a system of dichloromethane and methanol, n-hexane and ethyl acetate, petroleum ether and ethyl acetate, or acetone and the like, wherein the volume ratio of the solvents might be regulated according to the different polarity of compounds.

DMF refers to dimethylformamide, DMSO refers to dimethylsulfoxide, THF refers to tetrahydrofuran, DIEA refers to N,N-diisopropylethylamine, EA refers to ethyl acetate, PE refers to petroleum ether. BINAP refers to (2R, 3S)-2,2'-bis diphenylphosphino-1,1'-binaphthyl, NBS refers to N-bromosuccinimide, NCS refers to N-chlorosuccinimide, Pd2 (dba)3 refers to tris(dibenzylideneacetone)dipalladium, Pd(dppf)Cl2 refers to [1,1'-bis(diphenylphosphino)ferrocene]palladium dichloride.

As used herein, room temperature refers to be about 25° C.

Example 1: (Z)-5-(benzo[d][1,3]dioxol-5-ylmethylene)-2-(methyl(phenyl)amino)-3,5-dihydro-4H-imidazol-4-one

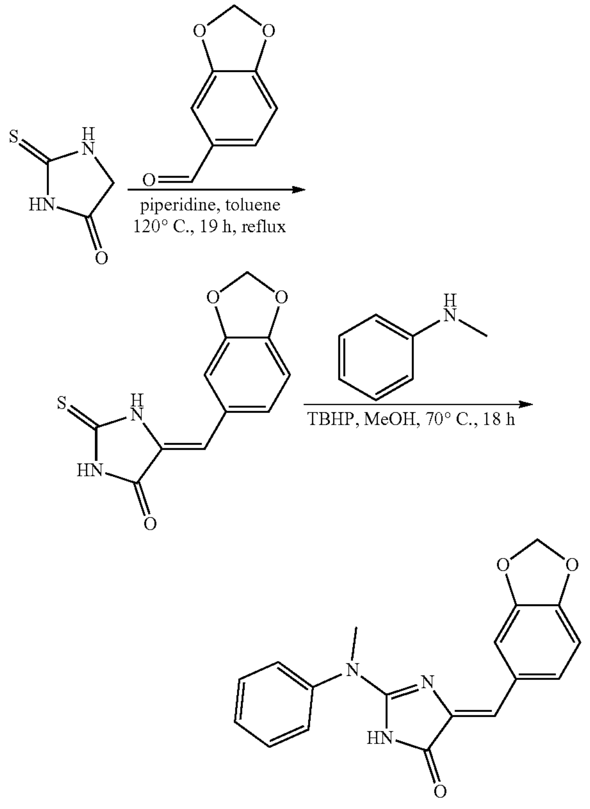

TJU-B115

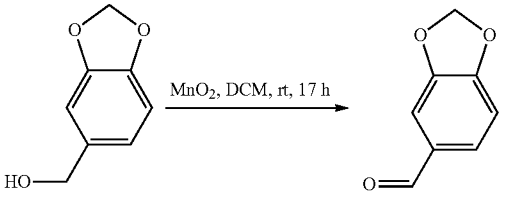

To a solution of benzo[d][1,3]dioxol-5-ylmethanol (10.0 g, 65.7 mmol) in DCM (150 mL) was added activated $MnO_2$ (57.0 g, 657 mmol) and the mixture was stirred at 40° C. for 17 h. After filtration, the filtrate was concentrated to afford benzo[d][1,3]dioxole-5-carbaldehyde (9.8 g, 99%) as a white solid which was used for the next step without further purification. LRMS (M+H$^+$) m/z calculated 151.0. found 151.0.

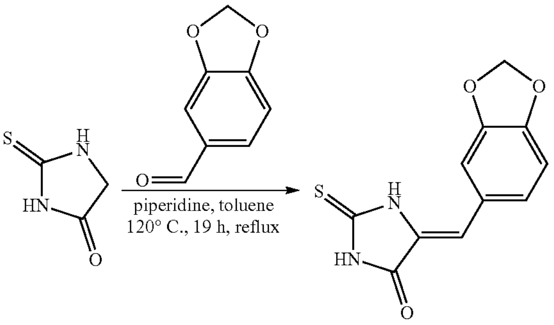

To a mixture of 2-thioxoimidazolidin-4-one (1.9 g, 17 mmol) and benzo[d][1,3]dioxole-5-carbaldehyde (3.0 g, 20.4 mmol) in toluene (30 mL) was added piperidine (71 mg, 0.85 mmol) and the mixture was stirred at 120° C. for 19 h. After concentration, the residue was recrystallized from DCM (30 mL) to afford (Z)-5-(benzo[d][1,3]dioxol-5-ylmethylene)-2-thioxoimidazolidin-4-one (3.8 g, 90%) as a yellow solid which was used for the next step without further purification. LRMS (M+H$^+$) m/z calculated 249.0. found 249.0.

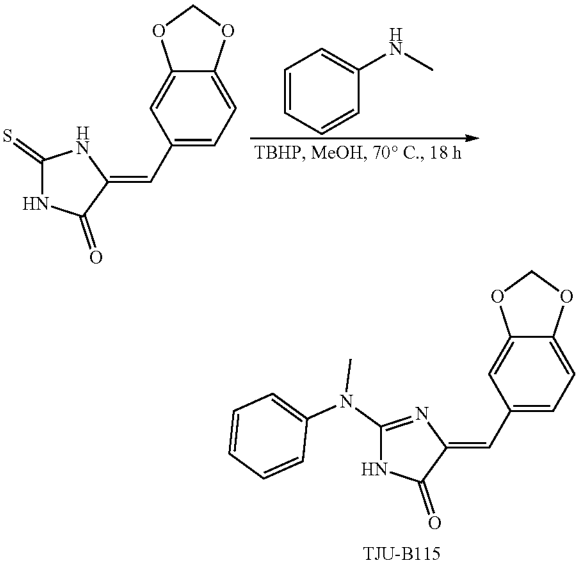

TJU-B115

To a mixture of (Z)-5-(benzo[d][1,3]dioxol-5-ylmethylene)-2-thioxoimidazolidin-4-one (600 mg, 2.4 mmol) and aniline (2235 mg, 24 mmol) in methanol (8 mL) was added a solution of TBHP (70% in water, 649 mg, 7.2 mmol) and the mixture was stirred at room temperature for 17 h. The reaction mixture was concentrated to remove excess aniline and the residue was recrystallized from MeOH (20 mL) to afford (Z)-5-(benzo[d][1,3]dioxol-5-ylmethylene)-2-

(methyl(phenyl)amino)-3,5-dihydro-4H-imidazol-4-one (65.0 mg, 35%) as a yellow solid. LRMS (M+H$^+$) m/z calculated 322.1. found 322.1. $^1$H NMR (400 MHz, DMSO-d6) δ 10.96 (s, 1H), 7.93 (d, J=1.4 Hz, 1H), 7.47-7.38 (m, 5H), 7.34-7.27 (m, 1H), 6.91 (d, J=8.0 Hz, 1H), 6.37 (s, 1H), 6.03 (s, 2H), 3.48 (s, 3H).

Example 2: (Z)-5-(benzo[d][1,3]dioxol-5-ylmethylene)-3-benzyl-2-(benzyl(phenyl)amino)-3,5-dihydro-4H-imidazol-4-one

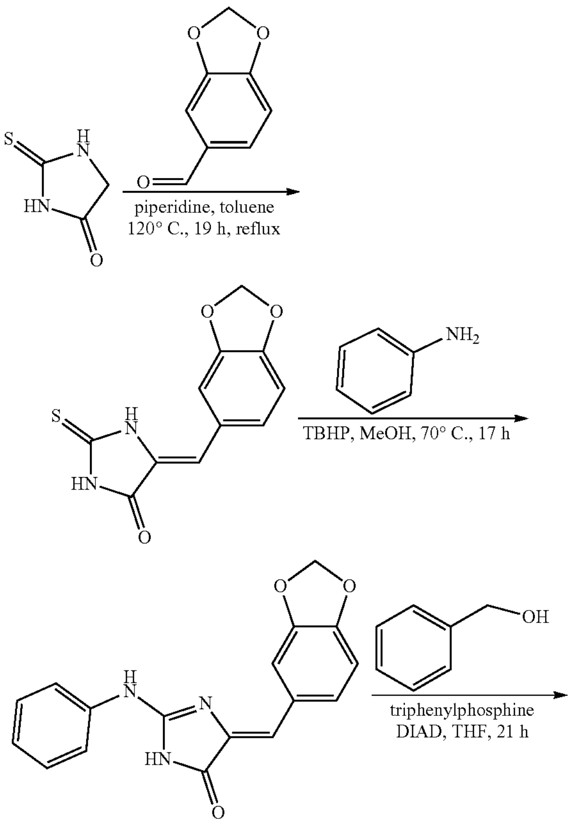

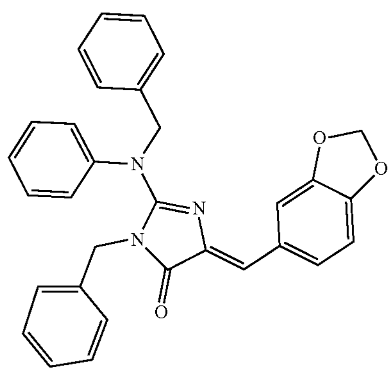

TJU-B076

-continued

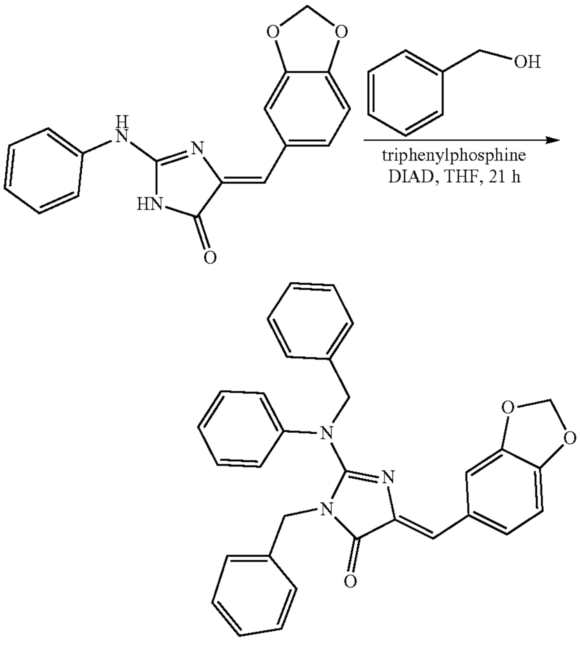

To a mixture of (Z)-5-(benzo[d][1,3]dioxol-5-ylmethylene)-2-(phenylamino)-3,5-dihydro-4H-imidazol-4-one (46 mg, 0.15 mmol), phenylmethanol (21 mg, 0.195 mmol) and triphenylphosphine (59 mg, 0.225 mmol) in THF (1 mL) was added DIAD (46 mg, 0.225 mmol) at room temperature. The mixture was stirred at room temperature for 21 h under $N_2$ protection. The reaction mixture was concentrated and the residue was purified by flash column chromatography on silica gel (EA/PE=1/1, v/v) to afford (Z)-5-(benzo[d][1,3]dioxol-5-ylmethylene)-3-benzyl-2-(benzyl(phenyl)amino)-3,5-dihydro-4H-imidazol-4-one (10 mg, 9%) as a yellow solid.

LRMS (M+H$^+$) m/z calculated 488.2. found 488.2. $^1$H NMR (400 MHz, DMSO-d6) δ 7.29-6.95 (m, 16H), 6.60 (t, J=20.0 Hz, 3H), 6.08 (s, 2H), 4.79 (s, 2H), 4.34 (s, 2H).

Example 3: (Z)-5-(benzo[d][1,3]dioxol-5-ylmethylene)-3-methyl-2-(methyl(phenyl)amino)-3,5-dihydro-4H-imidazol-4-one

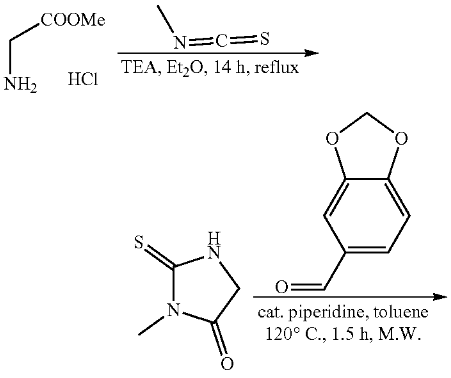

-continued

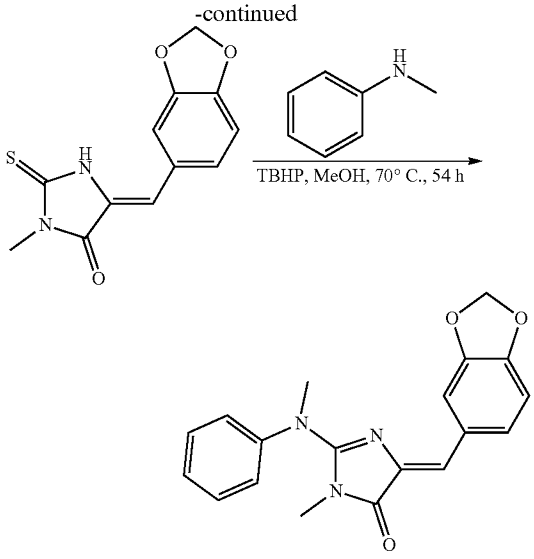

TJU-B116

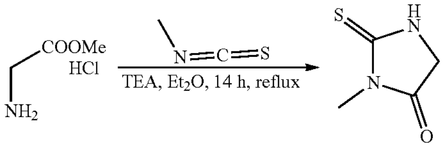

A suspension of methyl glycinate hydrochloride (10 g, 0.08 mol), methyl isothiocyanate (5.84 g, 0.08 mol), and triethylamine (8.08 g, 0.08 mol) in dry ether (150 mL) was stirred 38° C. for 14 h under $N_2$ atmosphere. The solvent was removed in vacuo, then EtOAc (200 mL) was added, the insoluble salt ($Et_3N$. HCl) was filtered off and the filtrate was concentrated and the residue was purified via column chromatography (DCM/MeOH=1/0 to 20/1, v/v) to give 3-methyl-2-thioxoimidazolidin-4-one (6.5 g, 63%) as a yellow solid. LRMS ($M+H^+$) m/z calculated 131.0. found 131.0. $^1H$ NMR (400 MHz, DMSO-d6) δ 7.53 (br, 1H), 4.10 (s, 2H), 3.26 (s, 3H).

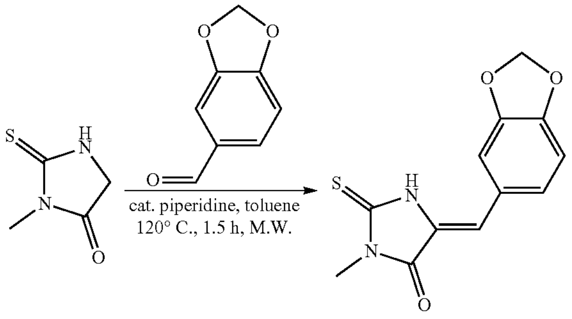

To a suspension of 3-methyl-2-thioxoimidazolidin-4-one (200 mg, 1.538 mmol) and 3,4-dimethoxybenzaldehyde (692 mg, 4.615 mmol) in toluene (5 mL) was added piperidine (7 mg, 0.076 mmol) and the reaction mixture was stirred at 120° C. for 1.5 h under microwave irradiation. The mixture was filtered and the filter cake was washed with $Et_2O$ to afford (Z)-5-(3,4-dimethoxybenzylidene)-3-methyl-2-thioxoimidazolidin-4-one (330 mg, 77%) as a yellow solid. LRMS ($M+H^+$) m/z calculated 263.1. found 263.1.

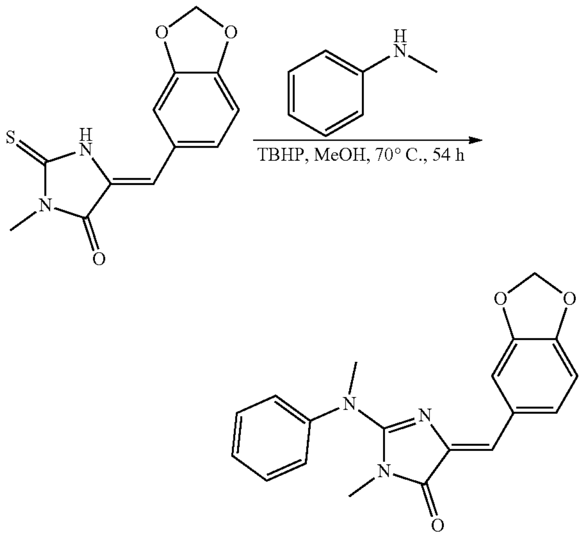

TJU-B116

To a mixture of (Z)-5-(benzo[d][1,3]dioxol-5-ylmethylene)-3-methyl-2-thioxoimidazolidin-4-one (628 mg, 2.4 mmol) and N-methylaniline (2568 mg, 24 mmol) in methanol (8 mL) was added a solution of TBHP (70% in water, 649 mg, 7.2 mmol). The mixture was stirred at room temperature for 17 h. The reaction mixture was concentrated to remove excess aniline and the residue was recrystallized from MeOH (20 mL) to afford (Z)-5-(benzo[d][1,3]dioxol-5-ylmethylene)-3-methyl-2-(methyl(phenyl)amino)-3,5-dihydro-4H-imidazol-4-one (53.0 mg). LRMS ($M+H^+$) m/z calculated 336.1. found 336.1. $^1H$ NMR (400 MHz, DMSO-d6) δ 8.02 (d, J=1.5 Hz, 1H), 7.55-7.53 (m, 1H), 7.49-7.45 (m, 2H), 7.36-7.31 (m, 3H), 6.98 (d, J=8.0 Hz, 1H), 6.64 (s, 1H), 6.07 (s, 2H), 3.50 (s, 3H), 2.44 (s, 3H).

Example 4: (Z)-5-(benzo[d][1,3]dioxol-5-ylmethylene)-2-(ethyl(phenyl)amino)-3,5-dihydro-4H-imidazol-4-one

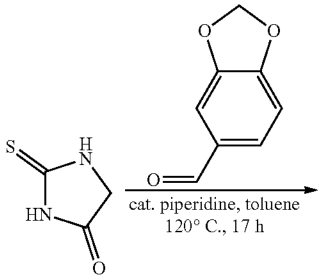

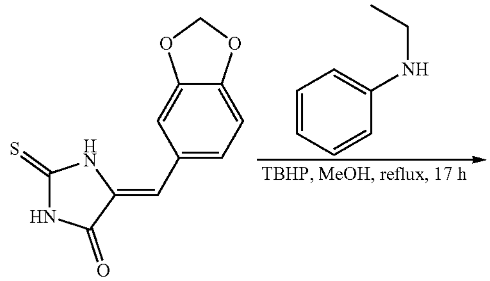

-continued

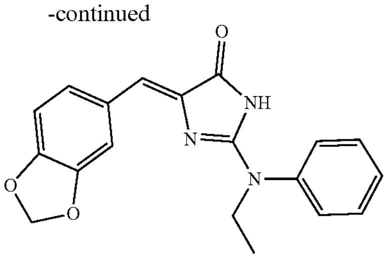

TJU-B182

(Z)-5-(benzo[d][1,3]dioxol-5-ylmethylene)-2-(ethyl(phenyl)amino)-3,5-dihydro-4H-imidazol-4-one (3.9 mg) was prepared in the same procedure as described for Example 1. LRMS (M+H$^+$) m/z calculated 336.1. found 336.2. $^1$H NMR (400 MHz, DMSO-d6) δ 10.82 (s, 1H), 7.92 (s, 1H), 7.49-7.46 (m, 2H), 7.38-7.34 (m, 4H), 6.91 (d, J=8.0 Hz, 1H), 6.34 (s, 1H), 6.02 (s, 2H), 3.95 (q, J=24 Hz, 2H), 1.16 (t, J=12 Hz, 3H).

Example 5: (Z)—N-(4-(benzo[d][1,3]dioxol-5-ylmethylene)-5-oxo-4,5-dihydro-1H-imidazol-2-yl)-N-phenylacetamide

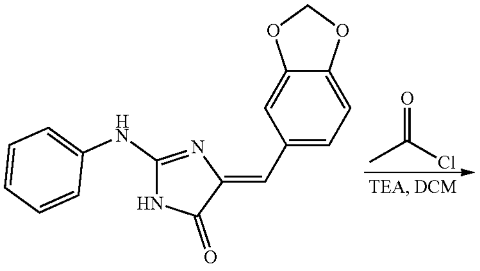

Leucettamine B, $L_{41}$
TJU-B038

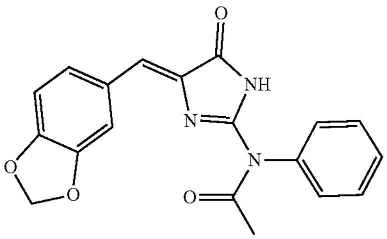

TJU-B183

To a solution of (Z)-5-(benzo[d][1,3]dioxol-5-ylmethylene)-2-(phenylamino)-3,5-dihydro-4H-imidazol-4-one (30 mg, 0.1 mmol, 1.0 equiv.) in DCM were added acetyl chloride (11.7 mg, 0.15 mmol, 1.5 equiv.) and TEA (30.3 mg, 0.3 mmol, 3.0 equiv.) at 0° C. The reaction mixture was stirred for 17 h at room temperature. After concentration, the residue was diluted with water and extracted with DCM (10 mL×3). The combined organic layer was dried over $Na_2SO_4$ and concentrated. The residue was triturated with (1 mL EA) to afford (Z)—N-(4-(benzo[d][1,3]dioxol-5-ylmethylene)-5-oxo-4,5-dihydro-1H-imidazol-2-yl)-N-phenylacetamide (5.3 mg, 17%) as a yellow solid. LRMS (M+H$^+$) m/z calculated 350.1. found 350.1. $^1$H NMR (400 MHz, DMSO-d6) δ 10.15 (s, 1H), 7.95 (s, 1H), 7.83 (d, J=8.0 Hz, 2H), 7.54 (d, J=8.0 Hz, 1H), 7.43 (t, J=16.0 Hz, 2H), 7.17 (t, J=16.0 Hz, 1H), 7.02 (d, J=8.0 Hz, 1H), 6.76 (s, 1H), 6.10 (s, 2H), 2.63 (s, 3H).

Example 6: Preparation of (Z)-5-(benzo[d][1,3]dioxol-5-ylmethylene)-2-(phenylamino)-3,5-dihydro-4H-imidazol-4-one, L-41

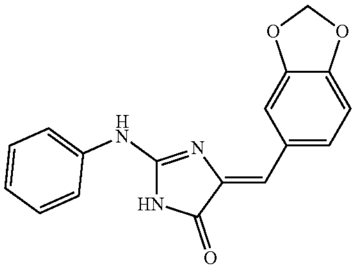

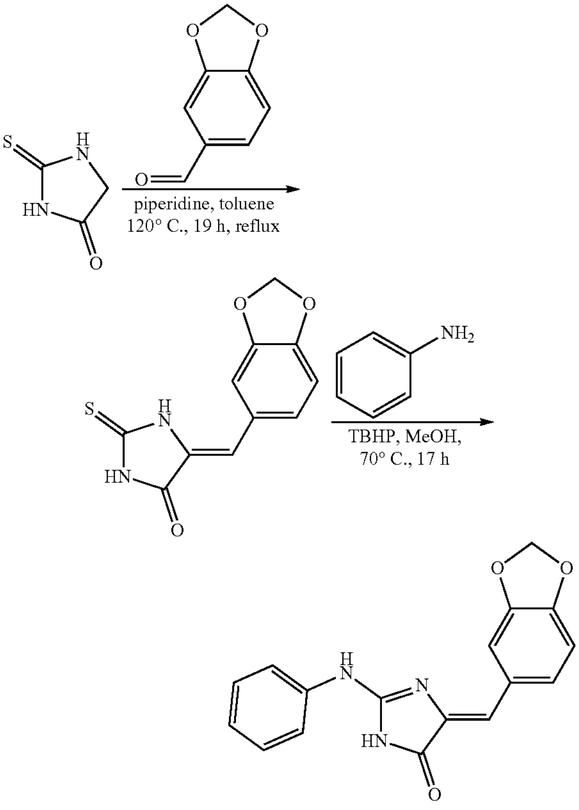

L41

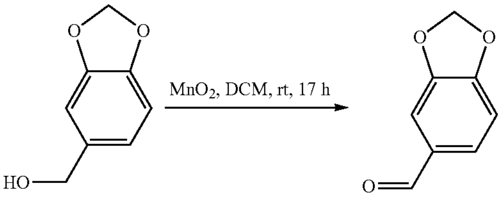

To a solution of benzo[d][1,3]dioxol-5-ylmethanol (10.0 g, 65.7 mmol, 1.0 eq.) in DCM (150 mL) was added activated $MnO_2$ (57.0 g, 657 mmol, 10 eq.). The mixture was stirred at 40° C. for 17 h. The reaction mixture was filtered and the filtrate was concentrated to afford benzo[d][1,3]dioxole-5-carbaldehyde (9.8 g, 99% yield) as a white solid which was used for the next step without further purification. LRMS (M+H$^+$) m/z calculated 151.0. found 151.0.

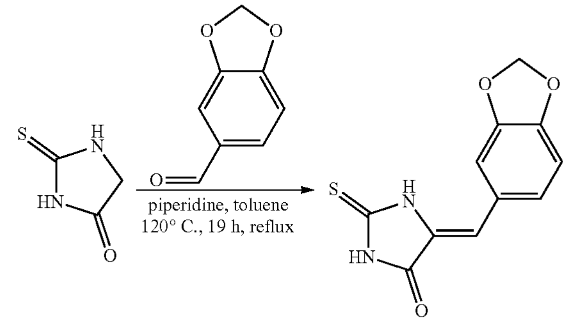

To a mixture of 2-thioxoimidazolidin-4-one (1.9 g, 17 mmol, 1.0 eq.) and benzo[d][1,3]dioxole-5-carbaldehyde (3.0 g, 20.4 mmol, 1.2 eq.) in toluene (30 mL) was added piperidine (71 mg, 0.85 mmol, 0.05 eq.). The mixture was stirred at 120° C. for 19 h, then concentrated. The residue was recrystallized from DCM (30 mL) and filtered to afford (Z)-5-(benzo[d][1,3]dioxol-5-ylmethylene)-2-thioxoimidazolidin-4-one (3.8 g, 90.13% yield) as a yellow solid which was used for the next step without further purification. LRMS (M+H$^+$) m/z calculated 249.0. found 249.0.

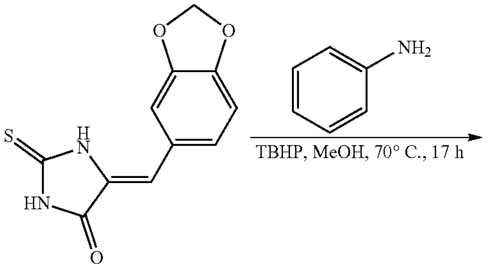

-continued

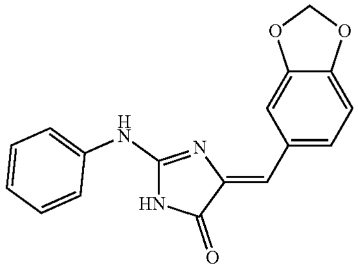

To a mixture of (Z)-5-(benzo[d][1,3]dioxol-5-ylmethylene)-2-thioxoimidazolidin-4-one (600 mg, 2.4 mmol, 1.0 eq.) and aniline (2235 mg, 24 mmol, 10.0 eq.) in methanol (8 mL) was added a solution of TBHP (70% in water, 649 mg, 7.2 mmol, 3.0 eq.). The mixture was stirred at rt for 17 h. The reaction mixture was concentrated to remove excess aniline and recrystallized from MeOH (20 mL) to afford (Z)-5-(benzo[d][1,3]dioxol-5-ylmethylene)-2-(phenylamino)-3,5-dihydro-4H-imidazol-4-one (643 mg, 87.25% yield) as a yellow solid. LRMS (M+H$^+$) m/z calculated 308.1. found 308.1.

$^1$H NMR (DMSO-d6, 400 MHz) δ 7.94 (br, 1H), 7.77 (d, J=8.0 Hz, 2H), 7.43 (d, J=4.0 Hz, 1H), 7.37 (t, J=16.0 Hz, 2H), 7.07 (t, J=12.0 Hz, 1H), 6.96 (d, J=12.0 Hz, 1H), 6.47 (s, 1H), 6.07 (s, 2H).

Example 7-53

The compounds in Table B were prepared in method that similar to Examples 1-6 with different starting compound. The data for the compounds of Examples 7-53 are listed in Table 1.

TABLE 1

| Example | Compound ID | Name |
|---|---|---|
| 7 | TJU-B001 | (4Z)-2-amino-1-methyl-4-[(naphthalen-2-yl)methylidene]-4,5-dihydro-1H-imidazol-5-one |
| 8 | TJU-B003 | (4Z)-2-amino-4-[(4-chlorophenyl)methylidene]-1-methyl-4,5-dihydro-1H-imidazol-5-one |
| 9 | TJU-B004 | (4Z)-4-[(2H-1,3-benzodioxol-5-yl)methylidene]-2-{[2-(morpholin-4-yl)ethyl]amino}-4,5-dihydro-1H-imidazol-5-one |
| 10 | TJU-B005 | 4-[(2H-1,3-benzodioxol-5-yl)methyl]-2-(phenylamino)-4,5-dihydro-1H-imidazol-5-one |
| 11 | TJU-B006 | (4Z)-4-[(2,3-dihydro-1,4-benzodioxin-6-yl)methylidene]-2-[(4-methoxyphenyl)amino]-4,5-dihydro-1H-imidazol-5-one |
| 12 | TJU-B007 | (4Z)-4-[(2,3-dihydro-1,4-benzodioxin-6-yl)methylidene]-2-(phenylamino)-4,5-dihydro-1H-imidazol-5-one |
| 13 | TJU-B009 | (4Z)-4-[(2H-1,3-benzodioxol-5-yl)methylidene]-2-[(4-methoxyphenyl)amino]-4,5-dihydro-1H-imidazol-5-one |
| 14 | TJU-B011 | (4Z)-4-[(6-chloro-2H-1,3-benzodioxol-5-yl)methylidene]-2-(phenylamino)-4,5-dihydro-1H-imidazol-5-one |
| 15 | TJU-B013 | (4Z)-4-[l-(2H-1,3-benzodioxol-5-yl)ethylidene]-2-(phenylamino)-4,5-dihydro-1H-imidazol-5-one |
| 16 | TJU-B014 | (4Z)-4-[(2H-1,3-benzodioxol-5-yl)methylidene]-1-methyl-2-(phenylamino)-4,5-dihydro-1H-imidazol-5-one |
| 17 | TJU-B016 | (4Z)-4-[(2H-1,3-benzodioxol-5-yl)methylidene]-1-methyl-2-[(propan-2-yl)amino]-4,5-dihydro-1H-imidazol-5-one |
| 18 | TJU-B019 | (4Z)-4-[(2H-1,3-benzodioxol-5-yl)methylidene]-2-(benzylamino)-4,5-dihydro-1H-imidazol-5-one |
| 19 | TJU-B021 | (4Z)-2-[(4-aminophenyl)amino]-4-[(2H-1,3-benzodioxol-5-yl)methylidene]-4,5-dihydro-1H-imidazol-5-one |

TABLE 1-continued

| Example | Compound ID | Name |
|---|---|---|
| 20 | TJU-B026 | (4Z)-4-[(2,3-dihydro-1,4-benzodioxin-6-yl)methylidene]-2-{[2-(morpholin-4-yl)ethyl] amino }-4,5-dihydro-1H-imidazol-5-one |
| 21 | TJU-B027 | (4Z)-2-[(2H-1,3-benzodioxol-5-yl)amino]-4-[(2H-1,3-benzodioxol-5-yl)methylidene]-4,5-dihydro-1H-imidazol-5-one |
| 22 | TJU-B028 | (4Z)-4-[(2,2-difluoro-2H-1,3-benzodioxol-5-yl)methylidene]-2-(phenylamino)-4,5-dihydro-1H-imidazol-5-one |
| 23 | TJU-B029 | (4Z)-4-[(2H-1,3-benzodioxol-5-yl)methylidene]-2-[(cyclopropylmethyl) amino]-4,5-dihydro-1H-imidazol-5-one |
| 24 | TJU-B031 | (4Z)-4-[(2H-1,3-benzodioxol-5-yl)methylidene]-2-[(pyridin-3-yl)amino]-4,5-dihydro-1H-imidazol-5-one |
| 25 | TJU-B033 | (4Z)-4-[(2H-1,3-benzodioxol-5-yl)methylidene]-2-(methylamino)-4,5-dihydro-1H-imidazol-5-one |
| 26 | TJU-B034 | (4Z)-2-amino-4-[(2H-1,3-benzodioxol-5-yl)methylidene]-4,5-dihydro-1H-imidazol-5-one |
| 27 | TJU-B036 | (4Z)-2-amino-4-[(3-methoxyphenyl)methylidene]-1-methyl-4,5-dihydro-1H-imidazol-5-one |
| 28 | TJU-B038 | (4Z)-4-[(2H-1,3-benzodioxol-5-yl)methylidene]-2-[(propan-2-yl)amino]-4,5-dihydro-1H-imidazol-5-one |
| 29 | TJU-B039 | (4Z)-4-[(2H-1,3-benzodioxol-5-yl)methylidene]-2-phenyl-4,5-dihydro-1H-imidazol-5-one |
| 30 | TJU-B040 | (4Z)-4-[(2H-1,3-benzodioxol-5-yl)methylidene]-2-(ethylamino)-4,5-dihydro-1H-imidazol-5-one |
| 31 | TJU-B043 | (4Z)-4-[(2H-1,3-benzodioxol-5-yl)methylidene]-2-(phenylamino)-4,5-dihydro-1H-imidazol-5-one |
| 32 | TJU-B045 | (4Z)-2-amino-1-methyl-4-(phenylmethylidene)-4,5-dihydro-1H-imidazol-5-one |
| 33 | TJU-B049 | (4Z)-2-amino-4-[(2,2-difluoro-2H-1,3-benzodioxol-5-yl)methylidene]-4,5-dihydro-1H-imidazol-5-one |
| 34 | TJU-B050 | (4Z)-2-amino-4-[(4-fluorophenyl)methylidene]-1-methyl-4,5-dihydro-1H-imidazol-5-one |
| 35 | TJU-B051 | (4Z)-4-[(7-methoxy-2H-1,3-benzodioxol-5-yl)methylidene]-2-(phenylamino)-4,5-dihydro-1H-imidazol-5-one |
| 36 | TJU-B052 | (4Z)-4-[(2H-1,3-benzodioxol-5-yl)methylidene]-2-[(cyclopropylmethyl) amino]-1-methyl-4,5-dihydro-1H-imidazol-5-one |
| 37 | TJU-B056 | (4Z)-2-amino-4-[(3-chlorophenyl)methylidene]-1-methyl-4,5-dihydro-1H-imidazol-5-one |
| 38 | TJU-B057 | (4Z)-2-amino-4-[(2H-1,3-benzodioxol-5-yl)methylidene]-1-methyl-4,5-dihydro-1H-imidazol-5-one |
| 39 | TJU-B058 | 4-{[(4Z)-4-[(2H-1,3-benzodioxol-5-yl)methylidene]-5-oxo-4,5-dihydro-1H-imidazol-2-yl] amino } benzonitrile |
| 40 | TJU-B059 | (4Z)-4-[(2H-1,3-benzodioxol-5-yl)methylidene]-2-cyclopropyl-4,5-dihydro-1H-imidazol-5-one |
| 41 | TJU-B060 | (4Z)-4-[(2H-1,3-benzodioxol-5-yl)methylidene]-2-[(4-chlorophenyl)amino]-4,5-dihydro-1H-imidazol-5-one |
| 42 | TJU-B063 | (4Z)-4-[(2,2-difluoro-2H-1,3-benzodioxol-5-yl)methylidene]-2-phenyl-4,5-dihydro-1H-imidazol-5-one |
| 43 | TJU-B064 | (4Z)-2-amino-4-[(6-chloro-2H-1,3-benzodioxol-5-yl)methylidene]-4,5-dihydro-1H-imidazo 1-5-one |
| 44 | TJU-B065 | (4Z)-2-amino-4-[(7-methoxy-2H-1,3-benzodioxol-5-yl)methylidene]-4,5-dihydro-1H-imidazol-5-one |
| 45 | TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| 46 | TJU-B067 | (4Z)-2-amino-4-[(2-fluorophenyl)methylidene]-1-methyl-4,5-dihydro-1H-imidazol-5-one |
| 47 | TJU-B070 | (4Z)-2-amino-4-[(3,4-dimethoxyphenyl)methylidene]-1-methyl-4,5-dihydro-1H-imidazol-5-one |
| 48 | TJU-B085 | (4Z)-4-[(3,4-dimethoxyphenyl)methylidene]-2-(phenylamino)-4,5-dihydro-1H-imidazol-5-one |
| 49 | TJU-B088 | (4Z)-2-[(2H-1,3-benzodioxol-5-yl)amino]-4-[(2H-1,3-benzodioxol-5-yl) methylidene]-1-methyl-4,5-dihydro-1H-imidazol-5-one |
| 50 | TJU-B097 | (4Z)-4-[(2H-1,3-benzodioxol-5-yl)methylidene]-2-[(pyridin-2-yl)amino]-4,5-dihydro-1H-imidazol-5-one |
| 51 | TJU-B110 | (4Z)-4-[(2H-1,3-benzodioxol-5-yl)methylidene]-2-[(4-methylphenyl)amino]-4,5-dihydro-1H-imidazol-5-one |
| 52 | TJU-B253 | (4Z)-4-[(2H-1,3-benzodioxol-5-yl)methylidene]-2-(cyclohexylamino)-4,5-dihydro-1H-imidazol-5-one |
| 53 | TJU-B254 | (4Z)-4-[(2H-1,3-benzodioxol-5-yl)methylidene]-2-[(2-methoxyphenyl) amino]-4,5-dihydro-1H-imidazol-5-one |

Test Example 1

(1) Assay Protocols

1. Isolation of and Culture Neonatal Rat Ventricular Myocytes (NRVMs)

Ventricles from neonatal rats were separated from the atria, cut into small pieces (about 2×2 $mm^2$) and then dissociated in $Ca^{2+}$-free HBSS containing 0.125 mg ml-1 trypsin (Gibco), 10 μg ml-1 DNase II (Sigma) and 0.1 mg ml-1 collagenase type IV (Sigma). The digestion was carried out under constant stirring at 37° C. for 5 min. The supernatant was collected with FBS (Gibco) after each digestion period. After digestion, the collected supernatant was centrifuged at 1000 g for 10 min at room temperature, and then cell pellets were resuspended in DMEM (Gibco) supplemented with 10% FBS and with 100 uM 5-bromo-2'-deoxyuridine (Sigma). The resuspended cells were passed through a cell strainer (100 mm, BD Falcon) and seeded onto 100-mm plastic dishes for 2 h at 37° C. in a 5% CO2 to remove fibroblasts, the supernatant was then collected and plated onto 1% gelatin (Sigma)-coated dishes. 24 h after the seeding, the medium was changed to DMEM (Gibco) containing 2% FBS (Gibco), 1% insulin-transferrin-selenium (ITS; Gibco), 1% Penicillin-Streptomycin (Gibco). After 24 hours of low serum culture, remove the medium with DMEM (Gibco) containing 6% FBS (Gibco), 1% insulin-transferrin-selenium (ITS; Gibco), 1% Penicillin-Streptomycin (Gibco), different concentrations of compounds (the compounds were pre-diluted in the medium and the drug concentration was 10 uM, 3 uM, 1 uM, fully mixed). After 36 h add Edu substrate (Invitrogen) according to the manufacturer's guidelines, and then after 12 h cell can be used.

2. EdU Assay 2.1. Immobilization: Remove the medium and fix the cells with 4 ul of PFA in 200 ul (whichever is covered) for 15 min and wash the cells twice with 500 ul of PBS for 5 min each time.

2.2. Broken membrane: Add 200 ul of 0.3% Triton-X 100 (diluted in PBS) to each well, incubate for 10-15 min at room temperature (the time should not be too long), and wash the cells twice with 500 ul of PBS for 5 min each time.

2.3. Blocking: Add 200 ul of 10% normal goat serum (diluted with 0.1% PBST) to each well, incubate for 1 h at room temperature, and wash twice with 500 ul of 0.1% PBST for 5 min each time.

2.4. Primary antibody: dilute the primary antibody (abcam, ab8295) to blocking solution at a ratio of 1:200, add 100 ul per well, incubate for 1 h at room temperature (may be slightly longer than 2-3 h), wash the cells twice with 500 ul 0.1% PBST for 5 min each time.

2.5. Secondary antibody: Dilute the fluorescently labeled secondary antibody (abcam, ab150117) into blocking solution at a ratio of 1:200, add 100 ul per well, incubate for 1 h at room temperature (the time should not be too long), wash the cells twice with 0.1% PBST for 5 min each time, pay attention to the whole process. Protected from light.

2.6. Edu staining (Invitrogen C10338)

2.6.1 Prepare Click-iT® reaction cocktail according to Table 3. It was important to add the ingredients in the order listed in the table; otherwise, the reaction would not proceed optimally. Use the Click-iT® reaction cocktail within 15 minutes of preparation.

TABLE 3

Click-IT ® reaction cocktails.

| Reaction components* | Number of coverslips 1 | 2 | 4 | 5 | 10 | 25 | 50 |
|---|---|---|---|---|---|---|---|
| 1× Click-IT ® reaction buffer (prepared in step 1.4) | 430 μL | 860 μL | 1.8 mL | 2.2 mL | 4.3 mL | 10.7 mL | 21.4 mL |
| $CuSO_4$ (Component E) | 20 μL | 40 μL | 80 μL | 100 μL | 200 μL | 500 μL | 1 mL |
| Alexa Fluor ® azide (prepared in step 1.3) | 1.2 μL | 2.5 μL | 5 μL | 6 μL | 12.5 μL | 31 μL | 62 μL |
| Reaction buffer additive (prepared in step 4.1) | 50 μL | 100 μL | 200 μL | 250 μL | 500 μL | 1.25 mL | 2.5 mL |
| Total volume | 500 μL | 1 mL | 2 mL | 2.5 mL | 5 mL | 12.5 mL | 25 mL |

*Note:
Add the ingredients in the order listed in the table.

2.6.2 Add 0.1 mL of Click-iT® reaction cocktail to each well containing a coverslip. Rock the plate briefly to ensure that the reaction cocktail is distributed evenly over the coverslip.

2.6.3 Incubate the plate for 30 minutes at room temperature, protected from light.

2.6.4 Remove the reaction cocktail, then wash the cells twice with 0.1% PBST for 5 min each time.

2.7. DAPI staining: DAPI stain was diluted to PBS at a ratio of 1:1000, 100 ul per well, incubated for 30 min at room temperature, and the cells were washed twice with PBS for 5 min each.

3. Data Analysis

We used Molecular Devices' Image Xpress Micro Confocal for high-throughput photo and data analysis.

Buffer Solution

1. PBS buffer: Take a volume of 500 ml as an example, 25 ml PBS buffer (20X) (Sangon Biotech, B548117-0500)+475 ml ddH2O 2. 0.1% PBST: Take a volume of 500 ml as an example, 25 ml PBS buffer (20X) (Sangon Biotech, B548117-0500)+475 ml ddH2O+500 ul Tween 20 (Sinopharm Chemical Reagent Co Ltd, 30189328)

References used for the cardiomyocyte proliferation assay:

1. Chen, J. et al. mir-17-92 cluster is required for and sufficient to induce cardiomyocyte proliferation in postnatal and adult hearts. Circ Res 112, 1557-1566, doi:10.1161/CIRCRESAHA.112.300658 (2013).
2. Andersson, O. et al. Adenosine signaling promotes regeneration of pancreatic beta cells in vivo. Cell Metab 15, 885-894, doi:10.1016/j.cmet.2012.04.018 (2012).
3. Dogra, D. et al. Opposite effects of Activin type 2 receptor ligands on cardiomyocyte proliferation during development and repair. Nat Commun 8, 1902, doi:10.1038/s41467-017-01950-1 (2017).
4. Hirose, K. et al. Evidence for hormonal control of heart regenerative capacity during endothermy acquisition. Science 364, 184-188, doi:10.1126/science.aar2038 (2019).
5. Lin, Z. et al. Pi3kcb links Hippo-YAP and PI3K-AKT signaling pathways to promote cardiomyocyte proliferation and survival. Circ Res 116, 35-45, doi:10.1161/CIRCRESAHA.115.304457 (2015).
6. Wang, J., Cao, J., Dickson, A. L. & Poss, K. D. Epicardial regeneration is guided by cardiac outflow tract and Hedgehog signalling. Nature 522, 226-230, doi:10.1038/nature14325 (2015).

7. Salic, A. & Mitchison, T. J. A chemical method for fast and sensitive detection of DNA synthesis in vivo. Proc Natl Acad Sci USA 105, 2415-2420, doi:10.1073/pnas.0712168105 (2008).

8. Wang, Q. et al. Bioconjugation by copper(I)-catalyzed azide-alkyne [3+2] cycloaddition. J Am Chem Soc 125, 3192-3193, doi:10.1021/ja021381e (2003).

(2) Results

The results of Test Example 1 are shown in Table 2

TABLE 2

| Average myocyte proliferation assay data | | | | |
|---|---|---|---|---|
| Compound ID | Example | Avg 1 uM | Avg 3 uM | Avg 10 uM |
| TJU-B115 | 1 | * | *** | ** |
| TJU-B076 | 2 | * | * | *** |
| TJU-B116 | 3 | * | * | * |
| TJU-B182 | 4 | ** | ** | ** |
| TJU-B183 | 5 | * | ** | *** |
| L41 | 6 | * | * | * |
| TJU-B001 | 7 | NT | NT | NT |
| TJU-B003 | 8 | NT | NT | NT |
| TJU-B004 | 9 | * | ** | *** |
| TJU-B005 | 10 | ** | * | *** |
| TJU-B006 | 11 | ** | ** | *** |
| TJU-B007 | 12 | * | ** | *** |
| TJU-B009 | 13 | ** | ** | *** |
| TJU-B011 | 14 | ** | ** | *** |
| TJU-B013 | 15 | * | ** | *** |
| TJU-B014 | 16 | * | ** | *** |
| TJU-B016 | 17 | * | ** | *** |
| TJU-B019 | 18 | * | * | *** |
| TJU-B021 | 19 | * | * | *** |
| TJU-B026 | 20 | ** | * | *** |
| TJU-B027 | 21 | * | * | ** |
| TJU-B028 | 22 | * | * | ** |
| TJU-B029 | 23 | * | * | ** |
| TJU-B031 | 24 | * | * | ** |
| TJU-B033 | 25 | * | * | ** |
| TJU-B034 | 26 | * | * | ** |
| TJU-B036 | 27 | ** | * | ** |
| TJU-B038 | 28 | ** | ** | ** |
| TJU-B039 | 29 | * | NT | ** |
| TJU-B040 | 30 | ** | ** | ** |
| TJU-B043 | 31 | ** | ** | ** |
| TJU-B045 | 32 | * | * | ** |
| TJU-B049 | 33 | ** | * | ** |
| TJU-B050 | 34 | * | * | ** |
| TJU-B051 | 35 | * | * | ** |
| TJU-B052 | 36 | ** | ** | ** |
| TJU-B056 | 37 | * | * | * |
| TJU-B057 | 38 | ** | * | * |
| TJU-B058 | 39 | ** | * | * |
| TJU-B059 | 40 | * | * | * |
| TJU-B060 | 41 | * | * | * |
| TJU-B063 | 42 | * | *** | * |
| TJU-B064 | 43 | * | * | * |
| TJU-B065 | 44 | * | * | * |
| TJU-B066 | 45 | ** | * | * |
| TJU-B067 | 46 | * | * | * |
| TJU-B070 | 47 | * | * | * |
| TJU-B085 | 48 | * | * | * |
| TJU-B088 | 49 | ** | * | * |
| TJU-B097 | 50 | * | * | * |
| TJU-B110 | 51 | ** | * | * |
| TJU-B253 | 52 | * | * | * |
| TJU-B254 | 53 | * | * | * |

Note:
*** => 50%,
** = 10%-50%,
* = <10% growth relative to blank myocyte growth without compound added.

Figure 3:
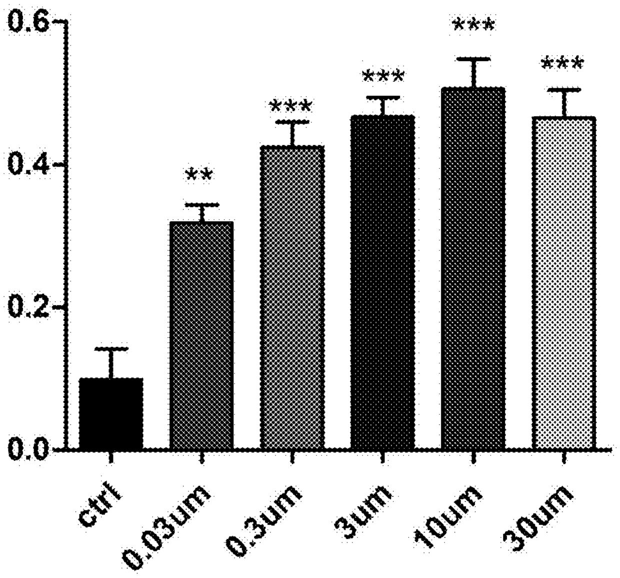
FIGS. 3 and 4 show compound L41 promotes myocyte growth.
Figure 4:
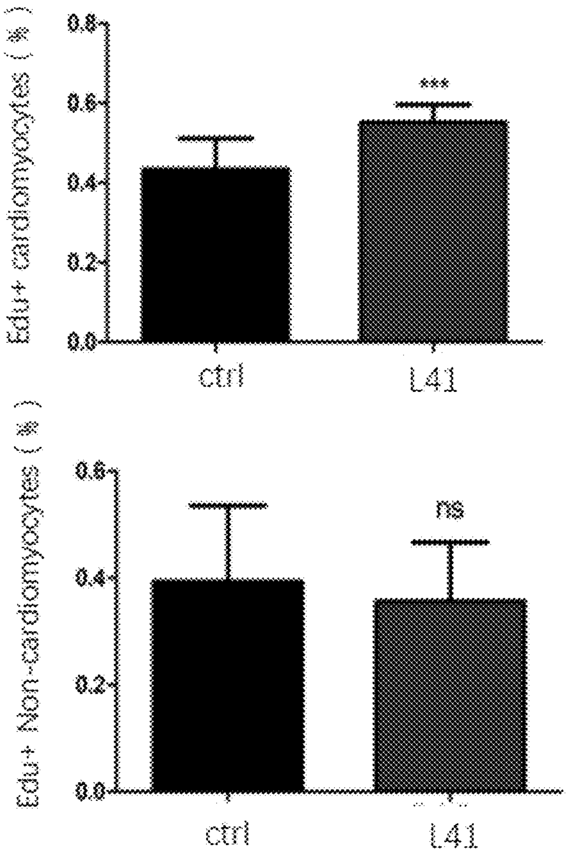

Activity data for compound L41 in myocyte growth assay is shown is FIGS. 3-4.

Figure 5:
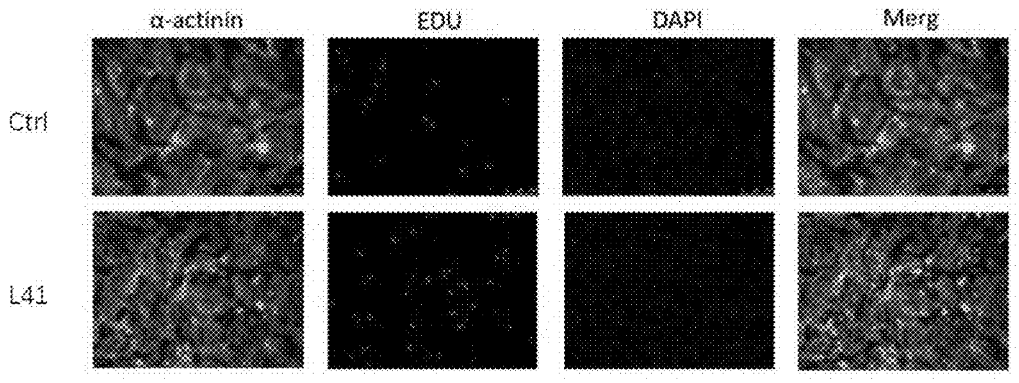
FIG. 5 shows the results of EDU proliferation index detection, which shows that small molecule compound L41 promotes proliferation of neonatal rat cardiomyocytes.

Myocyte growth detection for L41 under various assay conditions were tested. The result as shown in FIG. 5 indicated that L41 is a potent agonist for promoting myocyte growth or proliferation.

Test Example 2: Kinase Assay Methods

Compounds in the present invention have been evaluated for inhibition of human kinase activities in the following assays.

1. GSK3 Beta Enzyme Assay

The ability of compounds to inhibit human GSK3 beta kinase activities was determined using a commercially available ADP-Glo™ Kinase Assay kit (Promega, Cat #V9102) according to the manufacturer's protocol. The ADP-Glo™ Kinase Assay is a luminescent ADP detection assay that provides a universal, homogeneous, high-throughput screening method to measure kinase activity by quantifying the amount of ADP produced during a kinase reaction. The ADP-Glo™ Kinase Assay can be used to monitor the activity of virtually any ADP-generating enzymes (e.g., kinases or ATPases).

Recombinant full-length human GSK3 beta (expressed in Sf9 insect cells with an N-terminal His tag) was purchased from SignalChem (SignalChem, Cat #G09-10H). The GSK3 substrate peptide (sequence: YRRAAVPPSPSLSRHSSPHQ (pS)EDEEE) was purchased from SignalChem (SignalChem, Cat #G50-58). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the GSK3 substrate peptide are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, GSK3 beta (4 nM) in the enzymatic buffer solutions (40 mM Tris, 7.5, 20 mM $MgCl_2$, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 13 μM and 25 μM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

2. DYRK1A Enzyme Assay

The ability of compounds to inhibit human DYRK1A kinase activities was determined using a commercially available ADP-Glo™ Kinase Assay kit (Promega, Cat #V9102) according to the manufacturer's protocol.

Recombinant full-length DYRK1A (expressed in *E. coli* cells with an N-terminal GST tag) was purchased from SignalChem (SignalChem, Cat #D09-10G). The DYRK substrate peptide (DYRKtide, sequence: RRRFR-PASPLRGPPK) was purchased from SignalChem (SignalChem, Cat #D96-58). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the DYRKtide are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, DYRK1A (3 nM) in the enzymatic buffer solutions (40 mM Tris, 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 20 μM and 60 μM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

3. DYRK2 Enzyme Assay

The ability of compounds to inhibit human DYRK2 kinase activities was determined using a commercially available ADP-Glo™ Kinase Assay kit (Promega, Cat #V9102) according to the manufacturer's protocol.

Recombinant full-length human DYRK2 (expressed in *E. coli* cells with an N-terminal GST tag) was purchased from SignalChem (SignalChem, Cat #D10-10G). The DYRKtide peptide (sequence: RRRFRPASPLRGPPK) was purchased from SignalChem (SignalChem, Cat #D96-58). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the DYRKtide are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, DYRK2 (6 nM) in the enzymatic buffer solutions (40 mM Tris, 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 25 μM and 10 μM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

4. CLK1 Enzyme Assay

The ability of compounds to inhibit human CLK1 kinase activities was determined using a commercially available ADP-Glo™ Kinase Assay kit (Promega, Cat #V9102) according to the manufacturer's protocol.

Recombinant human CLK1 (129-end) (expressed in Sf9 insect cells with an N-terminal GST tag) was purchased from SignalChem (SignalChem, Cat #C57-11G). Recombinant full length human MBP (expressed in *E. coli* cells with an N-terminal GST tag.) was purchased from SignalChem (SignalChem, Cat #M42-54G). This assay, run in a 384-well plate format, is a generic method for measuring kinase activities using an ADP-Glo Kinase Assay Kit. The basic assay procedure involves two steps: (1) Enzymatic step: inhibitors are incubated with the kinase and then ATP (included in the ADP-Glo Kinase Assay Kit) and the MBP protein are added to start the enzymatic reaction; (2) Detection step: after the kinase reaction, first ADP-Glo™ Reagent is added to terminate the kinase reaction and deplete the remaining ATP. Second, the Kinase Detection Reagent is added to simultaneously convert ADP to ATP and allow the newly synthesized ATP to be measured using a luciferase/luciferin reaction. The light generated is measured using a luminometer.

Briefly, CLK1 (16 nM) in the enzymatic buffer solutions (40 mM Tris, 7.5, 20 mM MgCl2, 0.1 mg/ml BSA, 50 μM DTT) were mixed with various concentrations of inhibitors (dissolved in 100% DMSO). These solutions were incubated for 30 minutes at 25° C., and subsequently a mixture of substrate peptide and ATP was added with the final peptide and ATP concentrations at 2 μM and 10 μM, respectively. The final reaction mixture of enzyme-substrate-ATP-compound was incubated for 60 minutes at 25° C.

Afterwards ADP-Glo™ Reagent was added and the mixture was incubated at 25° C. for 60 minutes. Then Kinase Detection Reagent was added and the final mixture was incubated at 25° C. for 60 minutes. The luminescence signal of the final solution was measured on an Envision instrument (PerkinElmer). The percent (%) inhibition at each concentration of a compound is calculated relative to the luminescence signal in the Max and Min control wells contained within each assay plate. The Max control wells contain both enzyme and substrate as 0% inhibition, and the Min control wells only contain substrate without enzyme as 100% inhibition. The concentrations and percent inhibition values for a test compound are plotted and the concentration of the compound required to achieve 50% inhibition (IC50) is determined with a four-parameter logistic dose response equation.

5. Results

The results of test example 2 are shown in Table 4.

TABLE 4

Kinase activity of compounds

| Synthesis ID | Example | GSK3b IC50 (nM) | DYRKIA IC50 (nM) | CLKI IC50 (nM) |
|---|---|---|---|---|
| TJU-B115 | 1 | ++++ | ++ | ++ |
| TJU-B076 | 2 | ++++ | +++ | +++ |
| TJU-B116 | 3 | ++++ | +++ | +++ |
| TJU-B182 | 4 | ++++ | ++ | ++ |
| TJU-B183 | 5 | ++++ | + | ++ |

Data definition:
++++: >10000 nM,
+++: 1000-10000 nM,
++: 100-1000 nM,
+: <100 nM

Test Example 3: In Vivo Test

1. Myocardial Infarction 6-week-old C57/BL6 mice were anesthetized with 1% isoflurane in a chamber. The mice were placed in a left supine position on a heating pad (37° C.), and the heart was exposed via thoracotomy at the fourth left intercostal space. The pericardium was then opened, and the left coronary artery was permanently ligated with a 7-0 suture. Ligation was considered successful when the left ventricle became pale. From one week after surgery, the compound L41 or control solvent were injected via tail vein every other day. The mice were then euthanized after 6 weeks of injection, and the hearts were subjected to histology.

2. Injury Region Division

The cardiac tissue regions used for image characterization are described as the whole heart, infarct zone (left ventricle free wall), border zone (left ventricle anterior and posterior walls), or distal zone (interventricular septum).

3. Histology

For histology studies, hearts were collected at the indicated time points. After removing the blood by retrograde perfusion from the heart apex with cold PBS, the whole hearts were fixed with 4% paraformaldehyde (PFA, Sigma) at 4° C. overnight. Next, the hearts were dehydrated in increasing concentrations of ethanol and embedded in paraffin. Hematoxylin and eosin staining and Masson's trichrome staining were performed according to previously published methods [Development 140, 4683-4690 (2013)]

Hearts were sectioned at a thickness of 8 μm, and slides were created with 5 sections per slide. The sections started at the ligation site and ended at the heart apex (approximately 50 slides). Slides were stained with Masson's trichrome stain to identify areas of fibrosis. Scar size was quantified by examining serial sections from the apex to the ligation site and calculating the average percent fibrotic area of the total area using Image J software based on Masson's trichrome staining.

4. Results

Figure 6:
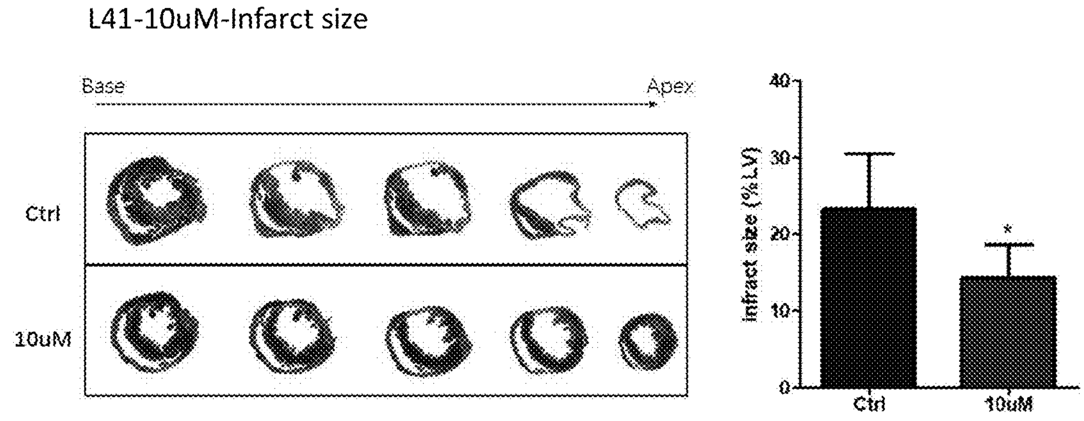
FIGS. 6 and 7 show the results of in vivo test of L41 in the heart Infarct model (10 uM and 30 uM).
Figure 7:
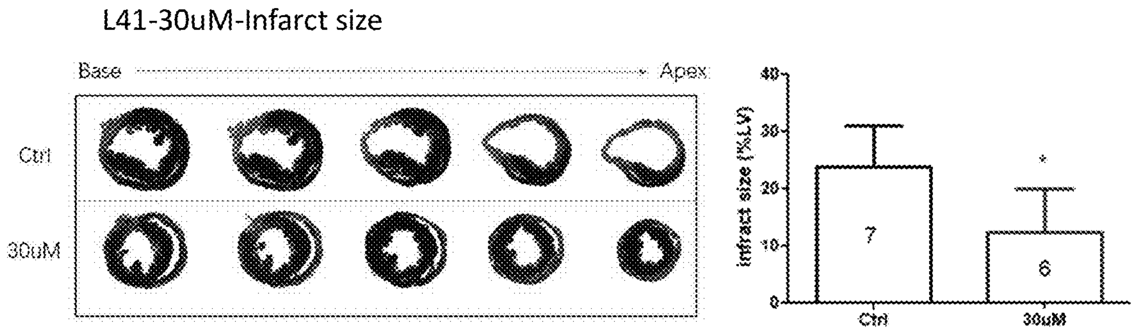

In vivo test showed that the compounds prepared in Examples 1-53 can promote cardiomyocyte proliferation in the heart Infarct model and reduced infarct size. Especially, L41 shows activity in the heart Infarct model where it is demonstrated to show reduction in infarct size (FIG. 6 and FIG. 7).

All publications mentioned herein are incorporated by reference as if each individual document was cited as a reference, as in the present application. It should also be understood that, after reading the above teachings of the present invention, those skilled in the art can make various changes or modifications, equivalents of which fall in the scope of claims as defined in the appended claims.

What is claimed:

1. A method for promoting growth of cardiomyocytes in vitro, which comprises a step of:

culturing cardiomyocyte in the present of a compound, or a pharmaceutically acceptable salt, a solvate, a stereoisomer or a prodrug;

wherein, the compound has a structure of Formula I:

(I)

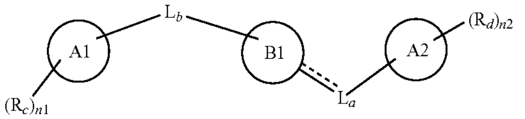

wherein $L_b$, ring B1 and $L_a$ together form

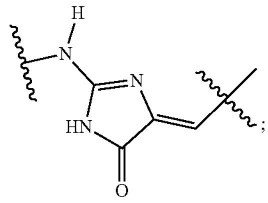 [SMILES: */C=C1\N=C(N*)NC1=O]

;

ring A1 is selected from the group consisting of C3-C10 heterocyclic group, C4-C10 heteroaryl, and C6-C10 aryl, wherein the heterocycle and heteroaryl each independently have 1-4 heteroatoms selected from N, O, and S;

ring A2 is

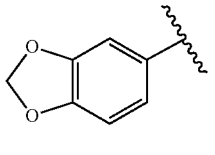

or

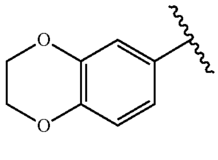

;

$R_c$ is selected from the group consisting of halogen, —OH, nitro, cyano, sulfonyl, R", —N(R")$_2$—, R"—O—, R"—S—, R"—S(O)$_2$—, R"—S(O)—, R"—C(O), R"—C(O)O—, and R"—OC(O)—; wherein each R" is independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl; and $R_d$ is selected from the group consisting of halogen, R", and R"—O—; wherein each R" is independently selected from the group consisting of H and C1-C6 alkyl;

n1 is 1, 2, 3, 4 or 5;

n2 is 0, 1, or 2;

or, the compound is selected from the group consisting of:

TJU-B115

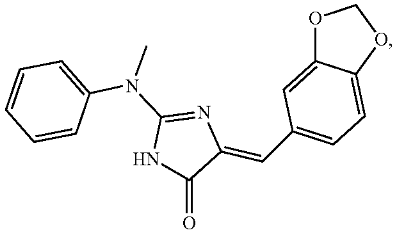

,

TJU-B076

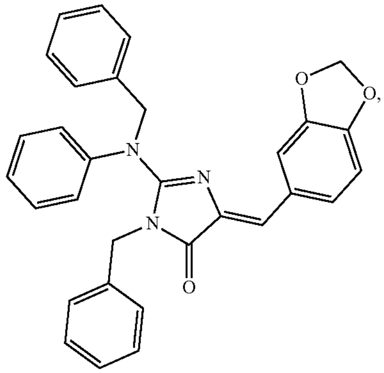

,

TJU-B-116

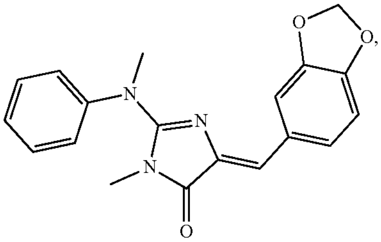

,

TJU-B182

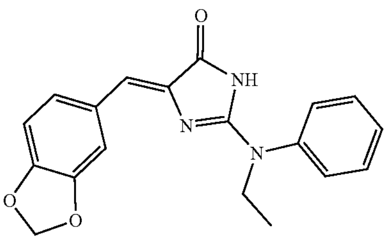

,

-continued

TJU-B183

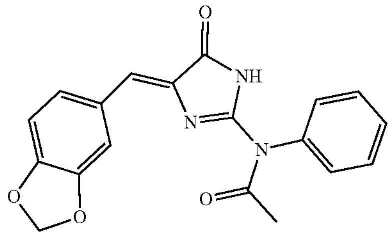

;

or, the compound is selected from the following table:

| Compound ID | Name |
|---|---|
| TJU-B004 | (4Z)-4-[(2H-1,3-benzodioxol-5-yl)methylidene]-2-{[2-(morpholin-4-yl)ethyl]amino}-4,5-dihydro-1H-imidazol-5-one |
| TJU-B005 | 4-[(2H-1,3-benzodioxol-5-yl)methyl]-2-(phenylamino)-4,5-dihydro-1H-imidazol-5-one |
| TJU-B006 | (4Z)-4-[(2,3-dihydro-1,4-benzodioxin-6-yl)methylidene]-2-[(4-methoxyphenyl)amino]-4,5-dihydro-1H-imidazol-5-one |
| TJU-B007 | (4Z)-4-[(2,3-dihydro-1,4-benzodioxin-6-yl)methylidene]-2-(phenylamino)-4,5-dihydro-1H-imidazol-5-one |
| TJU-B009 | (4Z)-4-[(2H-1,3-benzodioxol-5-yl)methylidene]-2-[(4-methoxyphenyl)amino]-4,5-dihydro-1H-imidazol-5-one |
| TJU-B011 | (4Z)-4-[(6-chloro-2H-1,3-benzodioxol-5-yl)methylidene]-2-(phenylamino)-4,5-dihydro-1H-imidazol-5-one |
| TJU-B013 | (4Z)-4-[1-(2H-1,3-benzodioxol-5-yl)ethylidene]-2-(phenylamino)-4,5-dihydro-1H-imidazol-5-one |
| TJU-B014 | (4Z)-4-[(2H-1,3-benzodioxol-5-yl)methylidene]-1-methyl-2-(phenylamino)-4,5-dihydro-1H-imidazol-5-one |
| TJU-B016 | (4Z)-4-[(2H-1,3-benzodioxol-5-yl)methylidene]-1-methyl-2-[(propan-2-yl)amino]-4,5-dihydro-1H-imidazol-5-one |
| TJU-B019 | (4Z)-4-[(2H-1,3-benzodioxol-5-yl)methylidene]-2-(benzylamino)-4,5-dihydro-1H-imidazol-5-one |
| TJU-B021 | (4Z)-2-[(4-aminophenyl)amino]-4-[(2H-1,3-benzodioxol-5-yl)methylidene]-4,5-dihydro-1H-imidazol-5-one |
| TJU-B026 | (4Z)-4-[(2,3-dihydro-1,4-benzodioxin-6-yl)methylidene]-2-{[2-(morpholin-4-yl)ethyl]amino}-4,5-dihydro-1H-imidazol-5-one |
| TJU-B027 | (4Z)-2-[(2H-1,3-benzodioxol-5-yl)amino]-4-[(2H-1,3-benzodioxol-5-yl)methylidene]-4,5-dihydro-1H-imidazol-5-one |
| TJU-B028 | (4Z)-4-[(2,2-difluoro-2H-1,3-benzodioxol-5-yl)methylidene]-2-(phenylamino)-4,5-dihydro-1H-imidazol-5-one |
| TJU-B029 | (4Z)-4-[(2H-1,3-benzodioxol-5-yl)methylidene]-2-[(cyclopropylmethyl)amino]-4,5-dihydro-1H-imidazol-5-one |
| TJU-B031 | (4Z)-4-[(2H-1,3-benzodioxol-5-yl)methylidene]-2-[(pyridin-3-yl)amino]-4,5-dihydro-1H-imidazol-5-one |
| TJU-B033 | (4Z)-4-[(2H-1,3-benzodioxol-5-yl)methylidene]-2-(methylamino)-4,5-dihydro-1H-imidazol-5-one |
| TJU-B034 | (4Z)-2-amino-4-[(2H-1,3-benzodioxol-5-yl)methylidene]-4,5-dihydro-1H-imidazol-5-one |
| TJU-B036 | (4Z)-2-amino-4-[(3-methoxyphenyl)methylidene]-1-methyl-4,5-dihydro-1H-imidazol-5-one |
| TJU-B038 | (4Z)-4-[(2H-1,3-benzodioxol-5-yl)methylidene]-2-[(propan-2-yl)amino]-4,5-dihydro-1H-imidazol-5-one |
| TJU-B039 | (4Z)-4-[(2H-1,3-benzodioxol-5-yl)methylidene]-2-phenyl-4,5-dihydro-1H-imidazol-5-one |
| TJU-B040 | (4Z)-4-[(2H-1,3-benzodioxol-5-yl)methylidene]-2-(ethylamino)-4,5-dihydro-1H-imidazol-5-one |
| TJU-B043 | (4Z)-4-[(2H-1,3-benzodioxol-5-yl)methylidene]-2-(phenylamino)-4,5-dihydro-1H-imidazol-5-one |
| TJU-B045 | (4Z)-2-amino-1-methyl-4-(phenylmethylidene)-4,5-dihydro-1H-imidazol-5-one |
| TJU-B049 | (4Z)-2-amino-4-[(2,2-difluoro-2H-1,3-benzodioxol-5-yl)methylidene]-4,5-dihydro-1H-imidazol-5-one |
| TJU-B050 | (4Z)-2-amino-4-[(4-fluorophenyl)methylidene]-1-methyl-4,5-dihydro-1H-imidazol-5-one |

-continued

| Compound ID | Name |
|---|---|
| TJU-B051 | (4Z)-4-[(7-methoxy-2H-1,3-benzodioxol-5-yl)methylidene]-2-(phenylamino)-4,5-dihydro-1H-imidazol-5-one |
| TJU-B052 | (4Z)-4-[(2H-1,3-benzodioxol-5-yl)methylidene]-2-[(cyclopropylmethyl)amino]-1-methyl-4,5-dihydro-1H-imidazol-5-one |
| TJU-B056 | (4Z)-2-amino-4-[(3-chlorophenyl)methylidene]-1-methyl-4,5-dihydro-1H-imidazol-5-one |
| TJU-B057 | (4Z)-2-amino-4-[(2H-1,3-benzodioxol-5-yl)methylidene]-1-methyl-4,5-dihydro-1H-imidazol-5-one |
| TJU-B058 | 4-{[(4Z)-4-[(2H-1,3-benzodioxol-5-yl)methylidene]-5-oxo-4,5-dihydro-1H-imidazol-2-yl]amino}benzonitrile |
| TJU-B059 | (4Z)-4-[(2H-1,3-benzodioxol-5-yl)methylidene]-2-cyclopropyl-4,5-dihydro-1H-imidazol-5-one |
| TJU-B060 | (4Z)-4-[(2H-1,3-benzodioxol-5-yl)methylidene]-2-[(4-chlorophenyl)amino]-4,5-dihydro-1H-imidazol-5-one |
| TJU-B063 | (4Z)-4-[(2,2-difluoro-2H-1,3-benzodioxol-5-yl)methylidene]-2-phenyl-4,5-dihydro-1H-imidazol-5-one |
| TJU-B064 | (4Z)-2-amino-4-[(6-chloro-2H-1,3-benzodioxol-5-yl)methylidene]-4,5-dihydro-1H-imidazol-5-one |
| TJU-B065 | (4Z)-2-amino-4-[(7-methoxy-2H-1,3-benzodioxol-5-yl)methylidene]-4,5-dihydro-1H-imidazol-5-one |
| TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| TJU-B067 | (4Z)-2-amino-4-[(2-fluorophenyl)methylidene]-1-methyl-4,5-dihydro-1H-imidazol-5-one |
| TJU-B070 | (4Z)-2-amino-4-[(3,4-dimethoxyphenyl)methylidene]-1-methyl-4,5-dihydro-1H-imidazol-5-one |
| TJU-B085 | (4Z)-4-[(3,4-dimethoxyphenyl)methylidene]-2-(phenylamino)-4,5-dihydro-1H-imidazol-5-one |
| TJU-B088 | (4Z)-2-[(2H-1,3-benzodioxol-5-yl)amino]-4-[(2H-1,3-benzodioxol-5-yl)methylidene]-1-methyl-4,5-dihydro-1H-imidazol-5-one |
| TJU-B097 | (4Z)-4-[(2H-1,3-benzodioxol-5-yl)methylidene]-2-[(pyridin-2-yl)amino]-4,5-dihydro-1H-imidazol-5-one |
| TJU-B110 | (4Z)-4-[(2H-1,3-benzodioxol-5-yl)methylidene]-2-[(4-methylphenyl)amino]-4,5-dihydro-1H-imidazol-5-one |
| TJU-B253 | (4Z)-4-[(2H-1,3-benzodioxol-5-yl)methylidene]-2-(cyclohexylamino)-4,5-dihydro-1H-imidazol-5-one |
| TJU-B254 | (4Z)-4-[(2H-1,3-benzodioxol-5-yl)methylidene]-2-[(2-methoxyphenyl)amino]-4,5-dihydro-1H-imidazol-5-one. |

2. The method of claim 1, wherein the compound is L41, a pharmaceutically acceptable salt, a solvate, a stereoisomer or a prodrug, or a derivative compound thereof:

L41

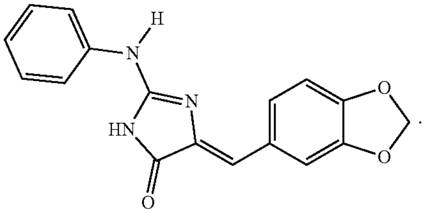

3. A method for promoting cardiomyocyte proliferation and/or regeneration of cardiomyocyte in vitro, which comprises a step of:

contacting cardiomyocyte with a compound, or a pharmaceutically acceptable salt, a solvate, a stereoisomer or a prodrug, thereby promoting cardiomyocyte proliferation and/or regeneration;

wherein the compound has a structure of Formula I:

(I)

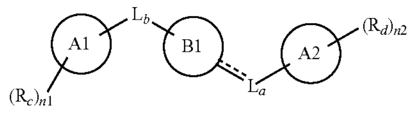

wherein $L_b$, ring B1 and $L_a$ together form

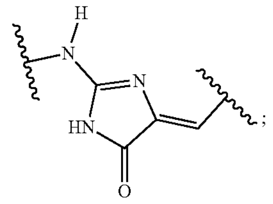 [SMILES: */C=C1\N=C(N*)NC1=O]

ring A1 is selected from the group consisting of C3-C10 heterocyclic group, C4-C10 heteroaryl, and C6-C10 aryl, wherein the heterocycle and heteroaryl each have 1-4 heteroatoms selected from N, O, and S;

ring A2 is

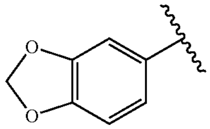

or

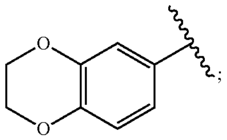

$R_c$ is selected from the group consisting of halogen, —OH, nitro, cyano, sulfonyl, R", —N(R")$_2$—, R"—O—, R"—S—, R"—S(O)$_2$—, R"—S(O)—, R"—C(O), R"—C(O)O—, and R"—OC(O)—; wherein each R" is independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl; and $R_d$ is selected from the group consisting of halogen, R", and R"—O—; wherein each R" is independently selected from the group consisting of H and C1-C6 alkyl;

n1 is 1, 2, 3, 4 or 5;

n2 is 0, 1, or 2;

or, the compound is selected from the group consisting of:

TJU-B115

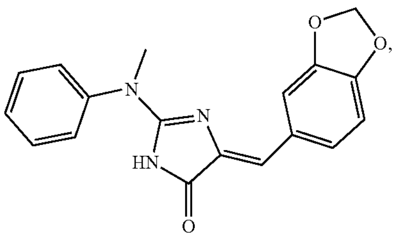

-continued

TJU-B076

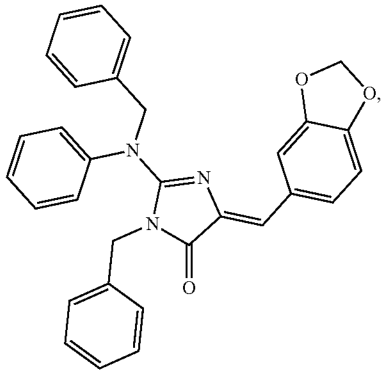

TJU-B-116

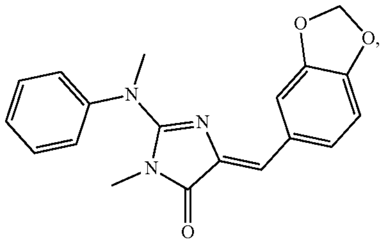

-continued

TJU-B182

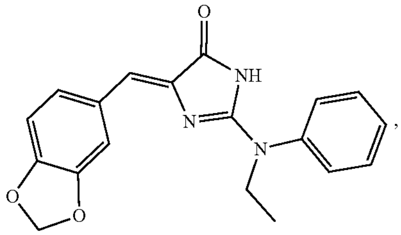

TJU-B183

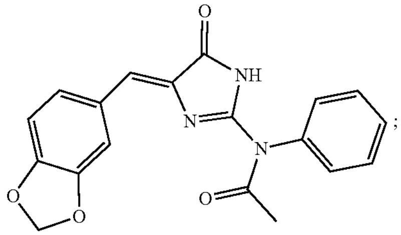

or, the compound is selected from the following table:

| Compound ID | Name |
|---|---|
| TJU-B004 | (4Z)-4-[(2H-1,3-benzodioxol-5-yl)methylidene]-2-{[2-(morpholin-4-yl)ethyl]amino}-4,5-dihydro-1H-imidazol-5-one |
| TJU-B005 | 4-[(2H-1,3-benzodioxol-5-yl)methyl]-2-(phenylamino)-4,5-dihydro-1H-imidazol-5-one |
| TJU-B006 | (4Z)-4-[(2,3-dihydro-1,4-benzodioxin-6-yl)methylidene]-2-[(4-methoxyphenyl)amino]-4,5-dihydro-1H-imidazol-5-one |
| TJU-B007 | (4Z)-4-[(2,3-dihydro-1,4-benzodioxin-6-yl)methylidene]-2-(phenylamino)-4,5-dihydro-1H-imidazol-5-one |
| TJU-B009 | (4Z)-4-[(2H-1,3-benzodioxol-5-yl)methylidene]-2-[(4-methoxyphenyl)amino]-4,5-dihydro-1H-imidazol-5-one |
| TJU-B011 | (4Z)-4-[(6-chloro-2H-1,3-benzodioxol-5-yl)methylidene]-2-(phenylamino)-4,5-dihydro-1H-imidazol-5-one |
| TJU-B013 | (4Z)-4-[1-(2H-1,3-benzodioxol-5-yl)ethylidene]-2-(phenylamino)-4,5-dihydro-1H-imidazol-5-one |
| TJU-B014 | (4Z)-4-[(2H-1,3-benzodioxol-5-yl)methylidene]-1-methyl-2-(phenylamino)-4,5-dihydro-1H-imidazol-5-one |
| TJU-B016 | (4Z)-4-[(2H-1,3-benzodioxol-5-yl)methylidene]-1-methyl-2-[(propan-2-yl)amino]-4,5-dihydro-1H-imidazol-5-one |
| TJU-B019 | (4Z)-4-[(2H-1,3-benzodioxol-5-yl)methylidene]-2-(benzylamino)-4,5-dihydro-1H-imidazol-5-one |
| TJU-B021 | (4Z)-2-[(4-aminophenyl)amino]-4-[(2H-1,3-benzodioxol-5-yl)methylidene]-4,5-dihydro-1H-imidazol-5-one |
| TJU-B026 | (4Z)-4-[(2,3-dihydro-1,4-benzodioxin-6-yl)methylidene]-2-{[2-(morpholin-4-yl)ethyl]amino}-4,5-dihydro-1H-imidazol-5-one |
| TJU-B027 | (4Z)-2-[(2H-1,3-benzodioxol-5-yl)amino]-4-[(2H-1,3-benzodioxol-5-yl)methylidene]-4,5-dihydro-1H-imidazol-5-one |
| TJU-B028 | (4Z)-4-[(2,2-difluoro-2H-1,3-benzodioxol-5-yl)methylidene]-2-(phenylamino)-4,5-dihydro-1H-imidazol-5-one |
| TJU-B029 | (4Z)-4-[(2H-1,3-benzodioxol-5-yl)methylidene]-2-[(cyclopropylmethyl)amino]-4,5-dihydro-1H-imidazol-5-one |
| TJU-B031 | (4Z)-4-[(2H-1,3-benzodioxol-5-yl)methylidene]-2-[(pyridin-3-yl)amino]-4,5-dihydro-1H-imidazol-5-one |
| TJU-B033 | (4Z)-4-[(2H-1,3-benzodioxol-5-yl)methylidene]-2-(methylamino)-4,5-dihydro-1H-imidazol-5-one |
| TJU-B034 | (4Z)-2-amino-4-[(2H-1,3-benzodioxol-5-yl)methylidene]-4,5-dihydro-1H-imidazol-5-one |
| TJU-B036 | (4Z)-2-amino-4-[(3-methoxyphenyl)methylidene]-1-methyl-4,5-dihydro-1H-imidazol-5-one |
| TJU-B038 | (4Z)-4-[(2H-1,3-benzodioxol-5-yl)methylidene]-2-[(propan-2-yl)amino]-4,5-dihydro-1H-imidazol-5-one |
| TJU-B039 | (4Z)-4-[(2H-1,3-benzodioxol-5-yl)methylidene]-2-phenyl-4,5-dihydro-1H-imidazol-5-one |
| TJU-B040 | (4Z)-4-[(2H-1,3-benzodioxol-5-yl)methylidene]-2-(ethylamino)-4,5-dihydro-1H-imidazol-5-one |

-continued

| Compound ID | Name |
|---|---|
| TJU-B043 | (4Z)-4-[(2H-1,3-benzodioxol-5-yl)methylidene]-2-(phenylamino)-4,5-dihydro-1H-imidazol-5-one |
| TJU-B045 | (4Z)-2-amino-1-methyl-4-(phenylmethylidene)-4,5-dihydro-1H-imidazol-5-one |
| TJU-B049 | (4Z)-2-amino-4-[(2,2-difluoro-2H-1,3-benzodioxol-5-yl)methylidene]-4,5-dihydro-1H-imidazol-5-one |
| TJU-B050 | (4Z)-2-amino-4-[(4-fluorophenyl)methylidene]-1-methyl-4,5-dihydro-1H-imidazol-5-one |
| TJU-B051 | (4Z)-4-[(7-methoxy-2H-1,3-benzodioxol-5-yl)methylidene]-2-(phenylamino)-4,5-dihydro-1H-imidazol-5-one |
| TJU-B052 | (4Z)-4-[(2H-1,3-benzodioxol-5-yl)methylidene]-2-[(cyclopropylmethyl)amino]-1-methyl-4,5-dihydro-1H-imidazol-5-one |
| TJU-B056 | (4Z)-2-amino-4-[(3-chlorophenyl)methylidene]-1-methyl-4,5-dihydro-1H-imidazol-5-one |
| TJU-B057 | (4Z)-2-amino-4-[(2H-1,3-benzodioxol-5-yl)methylidene]-1-methyl-4,5-dihydro-1H-imidazol-5-one |
| TJU-B058 | 4-{[(4Z)-4-[(2H-1,3-benzodioxol-5-yl)methylidene]-5-oxo-4,5-dihydro-1H-imidazol-2-yl]amino} benzonitrile |
| TJU-B059 | (4Z)-4-[(2H-1,3-benzodioxol-5-yl)methylidene]-2-cyclopropyl-4,5-dihydro-1H-imidazol-5-one |
| TJU-B060 | (4Z)-4-[(2H-1,3-benzodioxol-5-yl)methylidene]-2-[(4-chlorophenyl)amino]-4,5-dihydro-1H-imidazol-5-one |
| TJU-B063 | (4Z)-4-[(2,2-difluoro-2H-1,3-benzodioxol-5-yl)methylidene]-2-phenyl-4,5-dihydro-1H-imidazol-5-one |
| TJU-B064 | (4Z)-2-amino-4-[(6-chloro-2H-1,3-benzodioxol-5-yl)methylidene]-4,5-dihydro-1H-imidazol-5-one |
| TJU-B065 | (4Z)-2-amino-4-[(7-methoxy-2H-1,3-benzodioxol-5-yl)methylidene]-4,5-dihydro-1H-imidazol-5-one |
| TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| TJU-B067 | (4Z)-2-amino-4-[(2-fluorophenyl)methylidene]-1-methyl-4,5-dihydro-1H-imidazol-5-one |
| TJU-B070 | (4Z)-2-amino-4-[(3,4-dimethoxyphenyl)methylidene]-1-methyl-4,5-dihydro-1H-imidazol-5-one |
| TJU-B085 | (4Z)-4-[(3,4-dimethoxyphenyl)methylidene]-2-(phenylamino)-4,5-dihydro-1H-imidazol-5-one |
| TJU-B088 | (4Z)-2-[(2H-1,3-benzodioxol-5-yl)amino]-4-[(2H-1,3-benzodioxol-5-yl)methylidene]-1-methyl-4,5-dihydro-1H-imidazol-5-one |
| TJU-B097 | (4Z)-4-[(2H-1,3-benzodioxol-5-yl)methylidene]-2-[(pyridin-2-yl)amino]-4,5-dihydro-1H-imidazol-5-one |
| TJU-B110 | (4Z)-4-[(2H-1,3-benzodioxol-5-yl)methylidene]-2-[(4-methylphenyl)amino]-4,5-dihydro-1H-imidazol-5-one |
| TJU-B253 | (4Z)-4-[(2H-1,3-benzodioxol-5-yl)methylidene]-2-(cyclohexylamino)-4,5-dihydro-1H-imidazol-5-one |
| TJU-B254 | (4Z)-4-[(2H-1,3-benzodioxol-5-yl)methylidene]-2-[(2-methoxyphenyl)amino]-4,5-dihydro-1H-imidazol-5-one |

4. The method of claim 3, wherein the compound is L41, a pharmaceutically acceptable salt, a solvate, a stereoisomer or a prodrug, or a derivative compound thereof:

L41

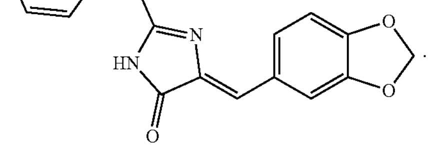

5. A method for treating a cardiovascular disease, which comprises a step of: administering a compound or a pharmaceutically acceptable salt, a solvate, a stereoisomer or a prodrug to a subject in need;

wherein the compound has a structure of Formula I:

(I)

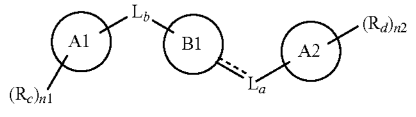

wherein $L_b$, ring B1 and $L_a$ together form

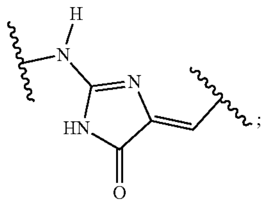 [SMILES: */C=C1\N=C(N*)NC1=O]

ring A1 is selected from the group consisting of C3-C10 heterocyclic group, C4-C10 heteroaryl, and C6-C10 aryl, wherein the heterocycle and heteroaryl each have 1-4 heteroatoms selected from N, O, and S;

ring A2 is

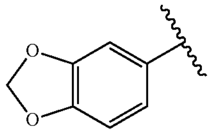

or

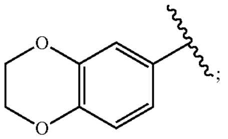

;

$R_c$ is selected from the group consisting of halogen, —OH, nitro, cyano, sulfonyl, R", —N(R")$_2$—, R"—O—, R"—S—, R"—S(O)$_2$—, R"—S(O)—, R"—C(O), R"—C(O)O—, and R"—OC(O)—; wherein each R" is independently selected from the group consisting of H, C1-C6 alkyl, C2-C6 alkenyl, C2-C6 alkynyl, C3-C8 cycloalkyl, C6-C10 aryl, 4- to 7-membered heterocycloalkyl, 5- to 7-membered heteroaryl, —C1-C4 alkylene-C3-C6 cycloalkyl, —C1-C4 alkylene-C6-C10 aryl, —C1-C4 alkylene-4 to 7-membered heterocycloalkyl, and —C1-C4 alkylene-5 to 7-membered heteroaryl; and $R_d$ is selected from the group consisting of halogen, R", and R"—O—; wherein R" is each independently selected from the group consisting of H, C1-C6 alkyl;

n1 is 1, 2, 3, 4 or 5;

n2 is 0, 1, or 2;

or, the compound is selected from the group consisting of:

TJU-B115

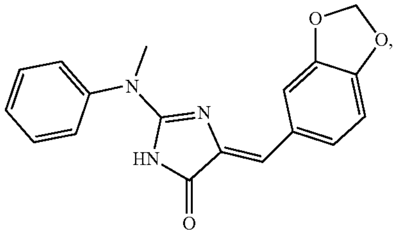

,

-continued

TJU-B076

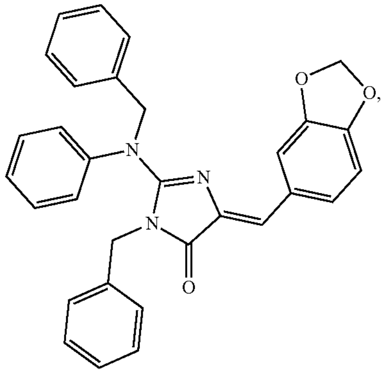

,

TJU-B-116

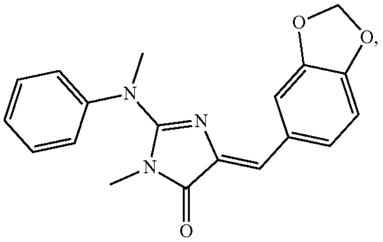

,

TJU-B182

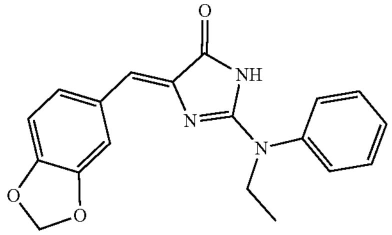

,

TJU-B183

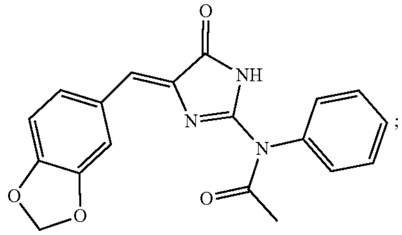

;

or, the compound is selected from the following table:

| Compound ID | Name |
|---|---|
| TJU-B004 | (4Z)-4-[(2H-1,3-benzodioxol-5-yl)methylidene]-2-{[2-(morpholin-4-yl)ethyl] amino}-4,5-dihydro-1H-imidazol-5-one |
| TJU-B005 | 4-[(2H-1,3-benzodioxol-5-yl)methyl]-2-(phenylamino)-4,5-dihydro-1H-imidazol-5-one |
| TJU-B006 | (4Z)-4-[(2,3-dihydro-1,4-benzodioxin-6-yl)methylidene]-2-[(4-methoxyphenyl) amino]-4,5-dihydro-1H-imidazol-5-one |
| TJU-B007 | (4Z)-4-[(2,3-dihydro-1,4-benzodioxin-6-yl)methylidene]-2-(phenylamino)-4,5-dihydro-1H-imidazol-5-one |
| TJU-B009 | (4Z)-4-[(2H-1,3-benzodioxol-5-yl)methylidene]-2-[(4-methoxyphenyl)amino]-4,5-dihydro-1H-imidazol-5-one |
| TJU-B011 | (4Z)-4-[(6-chloro-2H-1,3-benzodioxol-5-yl)methylidene]-2-(phenylamino)-4,5-dihydro-1H-imidazol-5-one |
| TJU-B013 | (4Z)-4-[1-(2H-1,3-benzodioxol-5-yl)ethylidene]-2-(phenylamino)-4,5-dihydro-1H-imidazol-5-one |
| TJU-B014 | (4Z)-4-[(2H-1,3-benzodioxol-5-yl)methylidene]-1-methyl-2-(phenylamino)-4,5-dihydro-1H-imidazol-5-one |
| TJU-B016 | (4Z)-4-[(2H-1,3-benzodioxol-5-yl)methylidene]-1-methyl-2-[(propan-2-yl) amino]-4,5-dihydro-1H-imidazol-5-one |

-continued

| Compound ID | Name |
|---|---|
| TJU-B019 | (4Z)-4-[(2H-1,3-benzodioxol-5-yl)methylidene]-2-(benzylamino)-4,5-dihydro-1H-imidazol-5-one |
| TJU-B021 | (4Z)-2-[(4-aminophenyl)amino]-4-[(2H-1,3-benzodioxol-5-yl)methylidene]-4,5-dihydro-1H-imidazol-5-one |
| TJU-B026 | (4Z)-4-[(2,3-dihydro-1,4-benzodioxin-6-yl)methylidene]-2-{[2-(morpholin-4-yl)ethyl]amino}-4,5-dihydro-1H-imidazol-5-one |
| TJU-B027 | (4Z)-2-[(2H-1,3-benzodioxol-5-yl)amino]-4-[(2H-1,3-benzodioxol-5-yl)methylidene]-4,5-dihydro-1H-imidazol-5-one |
| TJU-B028 | (4Z)-4-[(2,2-difluoro-2H-1,3-benzodioxol-5-yl)methylidene]-2-(phenylamino)-4,5-dihydro-1H-imidazol-5-one |
| TJU-B029 | (4Z)-4-[(2H-1,3-benzodioxol-5-yl)methylidene]-2-[(cyclopropylmethyl)amino]-4,5-dihydro-1H-imidazol-5-one |
| TJU-B031 | (4Z)-4-[(2H-1,3-benzodioxol-5-yl)methylidene]-2-[(pyridin-3-yl)amino]-4,5-dihydro-1H-imidazol-5-one |
| TJU-B033 | (4Z)-4-[(2H-1,3-benzodioxol-5-yl)methylidene]-2-(methylamino)-4,5-dihydro-1H-imidazol-5-one |
| TJU-B034 | (4Z)-2-amino-4-[(2H-1,3-benzodioxol-5-yl)methylidene]-4,5-dihydro-1H-imidazol-5-one |
| TJU-B036 | (4Z)-2-amino-4-[(3-methoxyphenyl)methylidene]-1-methyl-4,5-dihydro-1H-imidazol-5-one |
| TJU-B038 | (4Z)-4-[(2H-1,3-benzodioxol-5-yl)methylidene]-2-[(propan-2-yl)amino]-4,5-dihydro-1H-imidazol-5-one |
| TJU-B039 | (4Z)-4-[(2H-1,3-benzodioxol-5-yl)methylidene]-2-phenyl-4,5-dihydro-1H-imidazol-5-one |
| TJU-B040 | (4Z)-4-[(2H-1,3-benzodioxol-5-yl)methylidene]-2-(ethylamino)-4,5-dihydro-1H-imidazol-5-one |
| TJU-B043 | (4Z)-4-[(2H-1,3-benzodioxol-5-yl)methylidene]-2-(phenylamino)-4,5-dihydro-1H-imidazol-5-one |
| TJU-B045 | (4Z)-2-amino-1-methyl-4-(phenylmethylidene)-4,5-dihydro-1H-imidazol-5-one |
| TJU-B049 | (4Z)-2-amino-4-[(2,2-difluoro-2H-1,3-benzodioxol-5-yl)methylidene]-4,5-dihydro-1H-imidazol-5-one |
| TJU-B050 | (4Z)-2-amino-4-[(4-fluorophenyl)methylidene]-1-methyl-4,5-dihydro-1H-imidazol-5-one |
| TJU-B051 | (4Z)-4-[(7-methoxy-2H-1,3-benzodioxol-5-yl)methylidene]-2-(phenylamino)-4,5-dihydro-1H-imidazol-5-one |
| TJU-B052 | (4Z)-4-[(2H-1,3-benzodioxol-5-yl)methylidene]-2-[(cyclopropylmethyl)amino]-1-methyl-4,5-dihydro-1H-imidazol-5-one |
| TJU-B056 | (4Z)-2-amino-4-[(3-chlorophenyl)methylidene]-1-methyl-4,5-dihydro-1H-imidazol-5-one |
| TJU-B057 | (4Z)-2-amino-4-[(2H-1,3-benzodioxol-5-yl)methylidene]-1-methyl-4,5-dihydro-1H-imidazol-5-one |
| TJU-B058 | 4-{[(4Z)-4-[(2H-1,3-benzodioxol-5-yl)methylidene]-5-oxo-4,5-dihydro-1H-imid azol-2-yl]amino}benzonitrile |
| TJU-B059 | (4Z)-4-[(2H-1,3-benzodioxol-5-yl)methylidene]-2-cyclopropyl-4,5-dihydro-1H-imidazol-5-one |
| TJU-B060 | (4Z)-4-[(2H-1,3-benzodioxol-5-yl)methylidene]-2-[(4-chlorophenyl)amino]-4,5-dihydro-1H-imidazol-5-one |
| TJU-B063 | (4Z)-4-[(2,2-difluoro-2H-1,3-benzodioxol-5-yl)methylidene]-2-phenyl-4,5-dihydro-1H-imidazol-5-one |
| TJU-B064 | (4Z)-2-amino-4-[(6-chloro-2H-1,3-benzodioxol-5-yl)methylidene]-4,5-dihydro-1H-imidazol-5-one |
| TJU-B065 | (4Z)-2-amino-4-[(7-methoxy-2H-1,3-benzodioxol-5-yl)methylidene]-4,5-dihydro-1H-imidazol-5-one |
| TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| TJU-B067 | (4Z)-2-amino-4-[(2-fluorophenyl)methylidene]-1-methyl-4,5-dihydro-1H-imidazol-5-one |
| TJU-B070 | (4Z)-2-amino-4-[(3,4-dimethoxyphenyl)methylidene]-1-methyl-4,5-dihydro-1H-imidazol-5-one |
| TJU-B085 | (4Z)-4-[(3,4-dimethoxyphenyl)methylidene]-2-(phenylamino)-4,5-dihydro-1H-imidazol-5-one |
| TJU-B088 | (4Z)-2-[(2H-1,3-benzodioxol-5-yl)amino]-4-[(2H-1,3-benzodioxol-5-yl)methylidene]-1-methyl-4,5-dihydro-1H-imidazol-5-one |
| TJU-B097 | (4Z)-4-[(2H-1,3-benzodioxol-5-yl)methylidene]-2-[(pyridin-2-yl)amino]-4,5-dihydro-1H-imidazol-5-one |
| TJU-B110 | (4Z)-4-[(2H-1,3-benzodioxol-5-yl)methylidene]-2-[(4-methylphenyl)amino]-4,5-dihydro-1H-imidazol-5-one |
| TJU-B253 | (4Z)-4-[(2H-1,3-benzodioxol-5-yl)methylidene]-2-(cyclohexylamino)-4,5-dihydro-1H-imidazol-5-one |
| TJU-B254 | (4Z)-4-[(2H-1,3-benzodioxol-5-yl)methylidene]-2-[(2-methoxyphenyl)amino]-4,5-dihydro-1H-imidazol-5-one |

6. The method of claim 5, wherein the subjects comprises human and non-human mammal.

7. The method of claim 5, wherein the compound is L41, a pharmaceutically acceptable salt, a solvate, a stereoisomer or a prodrug, or a derivative compound thereof:

L41

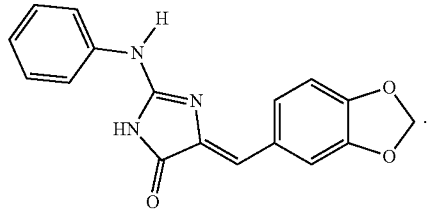

8. The method of claim 1, wherein the compound is selected from the group consisting of

TJU-B115

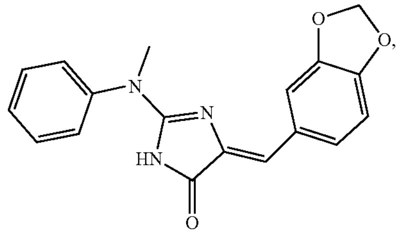

TJU-B076

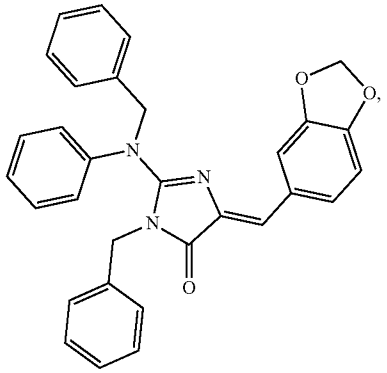

-continued

TJU-B182

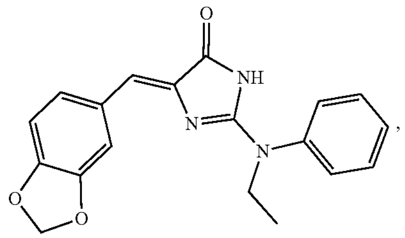

TJU-B183

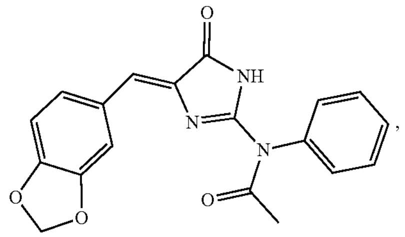

L41

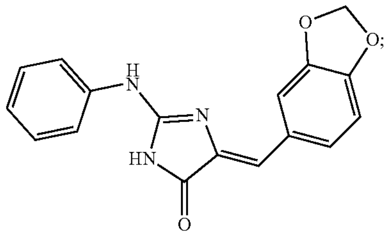

or the compound is selected from the following table

| Compound ID | Name |
|---|---|
| TJU-B004 | (4Z)-4-[(2H-1,3-benzodioxol-5-yl)methylidene]-2-{[2-(morpholin-4-yl)ethyl]amino}-4,5-dihydro-1H-imidazol-5-one |
| TJU-B005 | 4-[(2H-1,3-benzodioxol-5-yl)methyl]-2-(phenylamino)-4,5-dihydro-1H-imidazol-5-one |
| TJU-B006 | (4Z)-4-[(2,3-dihydro-1,4-benzodioxin-6-yl)methylidene]-2-[(4-methoxyphenyl)amino]-4,5-dihydro-1H-imidazol-5-one |
| TJU-B007 | (4Z)-4-[(2,3-dihydro-1,4-benzodioxin-6-yl)methylidene]-2-(phenylamino)-4,5-dihydro-1H-imidazol-5-one |
| TJU-B009 | (4Z)-4-[(2H-1,3-benzodioxol-5-yl)methylidene]-2-[(4-methoxyphenyl)amino]-4,5-dihydro-1H-imidazol-5-one |
| TJU-B011 | (4Z)-4-[(6-chloro-2H-1,3-benzodioxol-5-yl)methylidene]-2-(phenylamino)-4,5-dihydro-1H-imidazol-5-one |
| TJU-B013 | (4Z)-4-[1-(2H-1,3-benzodioxol-5-yl)ethylidene]-2-(phenylamino)-4,5-dihydro-1H-imidazol-5-one |
| TJU-B014 | (4Z)-4-[(2H-1,3-benzodioxol-5-yl)methylidene]-1-methyl-2-(phenylamino)-4,5-dihydro-1H-imidazol-5-one |
| TJU-B016 | (4Z)-4-[(2H-1,3-benzodioxol-5-yl)methylidene]-1-methyl-2-[(propan-2-yl)amino]-4,5-dihydro-1H-imidazol-5-one |
| TJU-B019 | (4Z)-4-[(2H-1,3-benzodioxol-5-yl)methylidene]-2-(benzylamino)-4,5-dihydro-1H-imidazol-5-one |

-continued

| Compound ID | Name |
|---|---|
| TJU-B021 | (4Z)-2-[(4-aminophenyl)amino]-4-[(2H-1,3-benzodioxol-5-yl)methylidene]-4,5-dihydro-1H-imidazol-5-one |
| TJU-B026 | (4,54Z)-4-[(2,3-dihydro-1,4-benzodioxin-6-yl)methylidene]-2-{[2-(morpholin-4-yl)ethyl]amino}-4,5-dihydro-1H-imidazol-5-one |
| TJU-B027 | (4Z)-2-[(2H-1,3-benzodioxol-5-yl)amino]-4-[(2H-1,3-benzodioxol-5-yl) methylidene]-4,5-dihydro-1H-imidazol-5-one |
| TJU-B028 | (4Z)-4-[(2,2-difluoro-2H-1,3-benzodioxol-5-yl)methylidene]-2-(phenylamino)-4,5-dihydro-1H-imidazol-5-one |
| TJU-B029 | (4Z)-4-[(2H-1,3-benzodioxol-5-yl)methylidene]-2-[(cyclopropylmethyl)amino]-4,5-dihydro-1H-imidazol-5-one |
| TJU-B031 | (4Z)-4-[(2H-1,3-benzodioxol-5-yl)methylidene]-2-[(pyridin-3-yl)amino]-4,5-dihydro-1H-imidazol-5-one |
| TJU-B033 | (4Z)-4-[(2H-1,3-benzodioxol-5-yl)methylidene]-2-(methylamino)-4,5-dihydro-1H-imidazol-5-one |
| TJU-B034 | (4Z)-2-amino-4-[(2H-1,3-benzodioxol-5-yl)methylidene]-4,5-dihydro-1H-imidazol-5-one |
| TJU-B036 | (4Z)-2-amino-4-[(3-methoxyphenyl)methylidene]-1-methyl-4,5-dihydro-1H-imidazol-5-one |
| TJU-B038 | (4Z)-4-[(2H-1,3-benzodioxol-5-yl)methylidene]-2-[(propan-2-yl)amino]-4,5-dihydro-1H-imidazol-5-one |
| TJU-B039 | (4Z)-4-[(2H-1,3-benzodioxol-5-yl)methylidene]-2-phenyl-4,5-dihydro-1H-imidazol-5-one |
| TJU-B040 | (4Z)-4-[(2H-1,3-benzodioxol-5-yl)methylidene]-2-(ethylamino)-4,5-dihydro-1H-imidazol-5-one |
| TJU-B043 | (4Z)-4-[(2H-1,3-benzodioxol-5-yl)methylidene]-2-(phenylamino)-4,5-dihydro-1H-imidazol-5-one |
| TJU-B045 | (4Z)-2-amino-1-methyl-4-(phenylmethylidene)-4,5-dihydro-1H-imidazol-5-one |
| TJU-B049 | (4Z)-2-amino-4-[(2,2-difluoro-2H-1,3-benzodioxol-5-yl)methylidene]-4,5-dihydro-1H-imidazol-5-one |
| TJU-B050 | (4Z)-2-amino-4-[(4-fluorophenyl)methylidene]-1-methyl-4,5-dihydro-1H-imidazol-5-one |
| TJU-B051 | (4Z)-4-[(7-methoxy-2H-1,3-benzodioxol-5-yl)methylidene]-2-(phenylamino)-4,5-dihydro-1H-imidazol-5-one |
| TJU-B052 | (4Z)-4-[(2H-1,3-benzodioxol-5-yl)methylidene]-2-[(cyclopropylmethyl)amino]-1-methyl-4,5-dihydro-1H-imidazol-5-one |
| TJU-B056 | (4Z)-2-amino-4-[(3-chlorophenyl)methylidene]-1-methyl-4,5-dihydro-1H-imidazol-5-one |
| TJU-B057 | (4Z)-2-amino-4-[(2H-1,3-benzodioxol-5-yl)methylidene]-1-methyl-4,5-dihydro-1H-imidazol-5-one |
| TJU-B058 | 4-{[(4Z)-4-[(2H-1,3-benzodioxol-5-yl)methylidene]-5-oxo-4,5-dihydro-1H-imidazol-2-yl]amino}benzonitrile |
| TJU-B059 | (4Z)-4-[(2H-1,3-benzodioxol-5-yl)methylidene]-2-cyclopropyl-4,5-dihydro-1H-imidazol-5-one |
| TJU-B060 | (4Z)-4-[(2H-1,3-benzodioxol-5-yl)methylidene]-2-[(4-chlorophenyl)amino]-4,5-dihydro-1H-imidazol-5-one |
| TJU-B063 | (4Z)-4-[(2,2-difluoro-2H-1,3-benzodioxol-5-yl)methylidene]-2-phenyl-4,5-dihydro-1H-imidazol-5-one |
| TJU-B064 | (4Z)-2-amino-4-[(6-chloro-2H-1,3-benzodioxol-5-yl)methylidene]-4,5-dihydro-1H-imidazol-5-one |
| TJU-B065 | (4Z)-2-amino-4-[(7-methoxy-2H-1,3-benzodioxol-5-yl)methylidene]-4,5-dihydro-1H-imidazol-5-one |
| TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| TJU-B067 | (4Z)-2-amino-4-[(2-fluorophenyl)methylidene]-1-methyl-4,5-dihydro-1H-imidazol-5-one |
| TJU-B070 | (4Z)-2-amino-4-[(3,4-dimethoxyphenyl)methylidene]-1-methyl-4,5-dihydro-1H-imidazol-5-one |
| TJU-B085 | (4Z)-4-[(3,4-dimethoxyphenyl)methylidene]-2-(phenylamino)-4,5-dihydro-1H-imidazol-5-one |
| TJU-B088 | (4Z)-2-[(2H-1,3-benzodioxol-5-yl)amino]-4-[(2H-1,3-benzodioxol-5-yl) methylidene]-1-methyl-4,5-dihydro-1H-imidazol-5-one |
| TJU-B097 | (4Z)-4-[(2H-1,3-benzodioxol-5-yl)methylidene]-2-[(pyridin-2-yl)amino]-4,5-dihydro-1H-imidazol-5-one |
| TJU-B110 | (4Z)-4-[(2H-1,3-benzodioxol-5-yl)methylidene]-2-[(4-methylphenyl)amino]-4,5-dihydro-1H-imidazol-5-one |
| TJU-B253 | (4Z)-4-[(2H-1,3-benzodioxol-5-yl)methylidene]-2-(cyclohexylamino)-4,5-dihydro-1H-imidazol-5-one |
| TJU-B254 | (4Z)-4-[(2H-1,3-benzodioxol-5-yl)methylidene]-2-[(2-methoxyphenyl)amino]-4,5-dihydro-1H-imidazol-5-one |

9. The method of claim 3, wherein the compound is selected from the group consisting of

TJU-B115

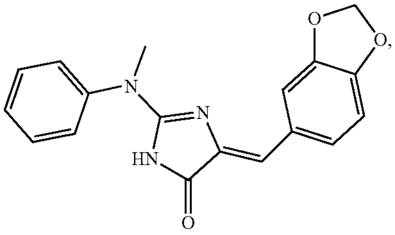

TJU-B076

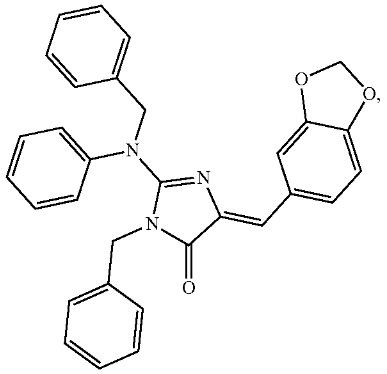

TJU-B182

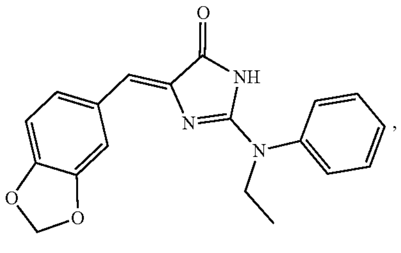

-continued

TJU-B183

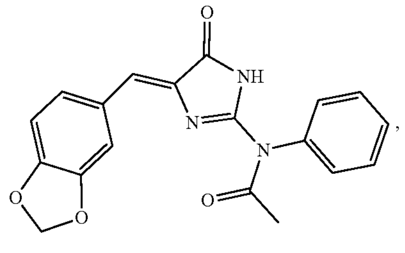

L41

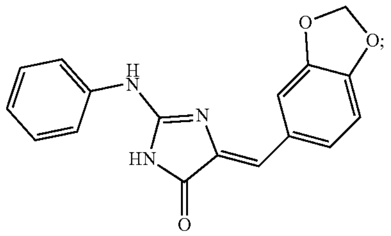

or the compound is selected from the following table

| Compound ID | Name |
|---|---|
| TJU-B004 | (4Z)-4-[(2H-1,3-benzodioxol-5-yl)methylidene]-2-{[2-(morpholin-4-yl)ethyl] amino}-4,5-dihydro-1H-imidazol-5-one |
| TJU-B005 | 4-[(2H-1,3-benzodioxol-5-yl)methyl]-2-(phenylamino)-4,5-dihydro-1H-imidazol-5-one |
| TJU-B006 | (4Z)-4-[(2,3-dihydro-1,4-benzodioxin-6-yl)methylidene]-2-[(4-methoxyphenyl) amino]-4,5-dihydro-1H-imidazol-5-one |
| TJU-B007 | (4Z)-4-[(2,3-dihydro-1,4-benzodioxin-6-yl)methylidene]-2-(phenylamino)-4,5-dihydro-1H-imidazol-5-one |
| TJU-B009 | (4Z)-4-[(2H-1,3-benzodioxol-5-yl)methylidene]-2-[(4-methoxyphenyl)amino]-4,5-dihydro-1H-imidazol-5-one |
| TJU-B011 | (4Z)-4-[(6-chloro-2H-1,3-benzodioxol-5-yl)methylidene]-2-(phenylamino)-4,5-dihydro-1H-imidazol-5-one |
| TJU-B013 | (4Z)-4-[1-(2H-1,3-benzodioxol-5-yl)ethylidene]-2-(phenylamino)-4,5-dihydro-1H-imidazol-5-one |
| TJU-B014 | (4Z)-4-[(2H-1,3-benzodioxol-5-yl)methylidene]-1-methyl-2-(phenylamino)-4,5-dihydro-1H-imidazol-5-one |
| TJU-B016 | (4Z)-4-[(2H-1,3-benzodioxol-5-yl)methylidene]-1-methyl-2-[(propan-2-yl) amino]-4,5-dihydro-1H-imidazol-5-one |
| TJU-B019 | (4Z)-4-[(2H-1,3-benzodioxol-5-yl)methylidene]-2-(benzylamino)-4,5-dihydro-1H-imidazol-5-one |
| TJU-B021 | (4Z)-2-[(4-aminophenyl)amino]-4-[(2H-1,3-benzodioxol-5-yl)methylidene]-4,5-dihydro-1H-imidazol-5-one |
| TJU-B026 | (4Z)-4-[(2,3-dihydro-1,4-benzodioxin-6-yl)methylidene]-2-{[2-(morpholin-4-yl)ethyl]amino}-4,5-dihydro-1H-imidazol-5-one |
| TJU-B027 | (4Z)-2-[(2H-1,3-benzodioxol-5-yl)amino]-4-[(2H-1,3-benzodioxol-5-yl) methylidene]-4,5-dihydro-1H-imidazol-5-one |
| TJU-B028 | (4Z)-4-[(2,2-difluoro-2H-1,3-benzodioxol-5-yl)methylidene]-2-(phenylamino)-4,5-dihydro-1H-imidazol-5-one |
| TJU-B029 | (4Z)-4-[(2H-1,3-benzodioxol-5-yl)methylidene]-2-[(cyclopropylmethyl)amino]-4,5-dihydro-1H-imidazol-5-one |

-continued

| Compound ID | Name |
|---|---|
| TJU-B031 | (4Z)-4-[(2H-1,3-benzodioxol-5-yl)methylidene]-2-[(pyridin-3-yl)amino]-4,5-dihydro-1H-imidazol-5-one |
| TJU-B033 | (4Z)-4-[(2H-1,3-benzodioxol-5-yl)methylidene]-2-(methylamino)-4,5-dihydro-1H-imidazol-5-one |
| TJU-B034 | (4Z)-2-amino-4-[(2H-1,3-benzodioxol-5-yl)methylidene]-4,5-dihydro-1H-imidazol-5-one |
| TJU-B036 | (4Z)-2-amino-4-[(3-methoxyphenyl)methylidene]-1-methyl-4,5-dihydro-1H-imidazol-5-one |
| TJU-B038 | (4Z)-4-[(2H-1,3-benzodioxol-5-yl)methylidene]-2-[(propan-2-yl)amino]-4,5-dihydro-1H-imidazol-5-one |
| TJU-B039 | (4Z)-4-[(2H-1,3-benzodioxol-5-yl)methylidene]-2-phenyl-4,5-dihydro-1H-imidazol-5-one |
| TJU-B040 | (4Z)-4-[(2H-1,3-benzodioxol-5-yl)methylidene]-2-(ethylamino)-4,5-dihydro-1H-imidazol-5-one |
| TJU-B043 | (4Z)-4-[(2H-1,3-benzodioxol-5-yl)methylidene]-2-(phenylamino)-4,5-dihydro-1H-imidazol-5-one |
| TJU-B045 | (4Z)-2-amino-1-methyl-4-(phenylmethylidene)-4,5-dihydro-1H-imidazol-5-one |
| TJU-B049 | (4Z)-2-amino-4-[(2,2-difluoro-2H-1,3-benzodioxol-5-yl)methylidene]-4,5-dihydro-1H-imidazol-5-one |
| TJU-B050 | (4Z)-2-amino-4-[(4-fluorophenyl)methylidene]-1-methyl-4,5-dihydro-1H-imidazol-5-one |
| TJU-B051 | (4Z)-4-[(7-methoxy-2H-1,3-benzodioxol-5-yl)methylidene]-2-(phenylamino)-4,5-dihydro-1H-imidazol-5-one |
| TJU-B052 | (4Z)-4-[(2H-1,3-benzodioxol-5-yl)methylidene]-2-[(cyclopropylmethyl)amino]-1-methyl-4,5-dihydro-1H-imidazol-5-one |
| TJU-B056 | (4Z)-2-amino-4-[(3-chlorophenyl)methylidene]-1-methyl-4,5-dihydro-1H-imidazol-5-one |
| TJU-B057 | (4Z)-2-amino-4-[(2H-1,3-benzodioxol-5-yl)methylidene]-1-methyl-4,5-dihydro-1H-imidazol-5-one |
| TJU-B058 | 4-{[(4Z)-4-[(2H-1,3-benzodioxol-5-yl)methylidene]-5-oxo-4,5-dihydro-1H-imidazol-2-yl]amino} benzonitrile |
| TJU-B059 | (4Z)-4-[(2H-1,3-benzodioxol-5-yl)methylidene]-2-cyclopropyl-4,5-dihydro-1H-imidazol-5-one |
| TJU-B060 | (4Z)-4-[(2H-1,3-benzodioxol-5-yl)methylidene]-2-[(4-chlorophenyl)amino]-4,5-dihydro-1H-imidazol-5-one |
| TJU-B063 | (4Z)-4-[(2,2-difluoro-2H-1,3-benzodioxol-5-yl)methylidene]-2-phenyl-4,5-dihydro-1H-imidazol-5-one |
| TJU-B064 | (4Z)-2-amino-4-[(6-chloro-2H-1,3-benzodioxol-5-yl)methylidene]-4,5-dihydro-1H-imidazol-5-one |
| TJU-B065 | (4Z)-2-amino-4-[(7-methoxy-2H-1,3-benzodioxol-5-yl)methylidene]-4,5-dihydro-1H-imidazol-5-one |
| TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| TJU-B067 | (4Z)-2-amino-4-[(2-fluorophenyl)methylidene]-1-methyl-4,5-dihydro-1H-imidazol-5-one |
| TJU-B070 | (4Z)-2-amino-4-[(3,4-dimethoxyphenyl)methylidene]-1-methyl-4,5-dihydro-1H-imidazol-5-one |
| TJU-B085 | (4Z)-4-[(3,4-dimethoxyphenyl)methylidene]-2-(phenylamino)-4,5-dihydro-1H-imidazol-5-one |
| TJU-B088 | (4Z)-2-[(2H-1,3-benzodioxol-5-yl)amino]-4-[(2H-1,3-benzodioxol-5-yl) methylidene]-1-methyl-4,5-dihydro-1H-imidazol-5-one |
| TJU-B097 | (4Z)-4-[(2H-1,3-benzodioxol-5-yl)methylidene]-2-[(pyridin-2-yl)amino]-4,5-dihydro-1H-imidazol-5-one |
| TJU-B110 | (4Z)-4-[(2H-1,3-benzodioxol-5-yl)methylidene]-2-[(4-methylphenyl)amino]-4,5-dihydro-1H-imidazol-5-one |
| TJU-B253 | (4Z)-4-[(2H-1,3-benzodioxol-5-yl)methylidene]-2-(cyclohexylamino)-4,5-dihydro-1H-imidazol-5-one |
| TJU-B254 | (4Z)-4-[(2H-1,3-benzodioxol-5-yl)methylidene]-2-[(2-methoxyphenyl)amino]-4,5-dihydro-1H-imidazol-5-one |

10. The method of claim 5, wherein the compound is selected from the group consisting of

TJU-B115

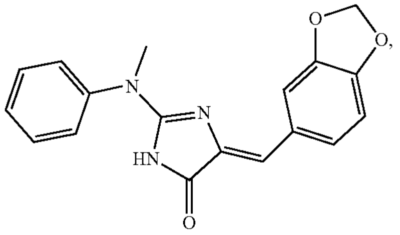

TJU-B076

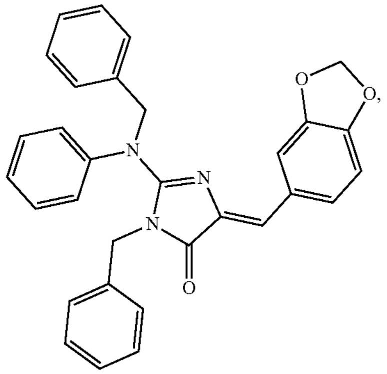

TJU-B182

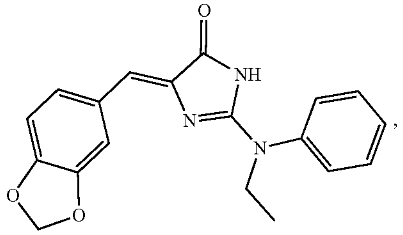

-continued

TJU-B183

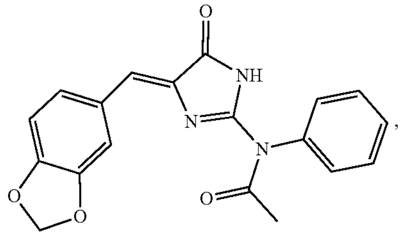

L41

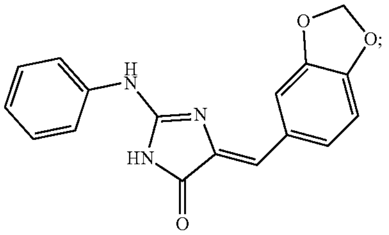

or the compound is selected from the following table

| Compound ID | Name |
|---|---|
| TJU-B004 | (4Z)-4-[(2H-1,3-benzodioxol-5-yl)methylidene]-2-{[2-(morpholin-4-yl)ethyl]amino}-4,5-dihydro-1H-imidazol-5-one |
| TJU-B005 | 4-[(2H-1,3-benzodioxol-5-yl)methyl]-2-(phenylamino)-4,5-dihydro-1H-imidazol-5-one |
| TJU-B006 | (4Z)-4-[(2,3-dihydro-1,4-benzodioxin-6-yl)methylidene]-2-[(4-methoxyphenyl)amino]-4,5-dihydro-1H-imidazol-5-one |
| TJU-B007 | (4Z)-4-[(2,3-dihydro-1,4-benzodioxin-6-yl)methylidene]-2-(phenylamino)-4,5-dihydro-1H-imidazol-5-one |
| TJU-B009 | (4Z)-4-[(2H-1,3-benzodioxol-5-yl)methylidene]-2-[(4-methoxyphenyl)amino]-4,5-dihydro-1H-imidazol-5-one |
| TJU-B011 | (4Z)-4-[(6-chloro-2H-1,3-benzodioxol-5-yl)methylidene]-2-(phenylamino)-4,5-dihydro-1H-imidazol-5-one |
| TJU-B013 | (4Z)-4-[1-(2H-1,3-benzodioxol-5-yl)ethylidene]-2-(phenylamino)-4,5-dihydro-1H-imidazol-5-one |
| TJU-B014 | (4Z)-4-[(2H-1,3-benzodioxol-5-yl)methylidene]-1-methyl-2-(phenylamino)-4,5-dihydro-1H-imidazol-5-one |
| TJU-B016 | (4Z)-4-[(2H-1,3-benzodioxol-5-yl)methylidene]-1-methyl-2-[(propan-2-yl)amino]-4,5-dihydro-1H-imidazol-5-one |
| TJU-B019 | (4Z)-4-[(2H-1,3-benzodioxol-5-yl)methylidene]-2-(benzylamino)-4,5-dihydro-1H-imidazol-5-one |
| TJU-B021 | (4Z)-2-[(4-aminophenyl)amino]-4-[(2H-1,3-benzodioxol-5-yl)methylidene]-4,5-dihydro-1H-imidazol-5-one |
| TJU-B026 | (4Z)-4-[(2,3-dihydro-1,4-benzodioxin-6-yl)methylidene]-2-{[2-(morpholin-4-yl)ethyl]amino}-4,5-dihydro-1H-imidazol-5-one |
| TJU-B027 | (4Z)-2-[(2H-1,3-benzodioxol-5-yl)amino]-4-[(2H-1,3-benzodioxol-5-yl)methylidene]-4,5-dihydro-1H-imidazol-5-one |
| TJU-B028 | (4Z)-4-[(2,2-difluoro-2H-1,3-benzodioxol-5-yl)methylidene]-2-(phenylamino)-4,5-dihydro-1H-imidazol-5-one |
| TJU-B029 | (4Z)-4-[(2H-1,3-benzodioxol-5-yl)methylidene]-2-[(cyclopropylmethyl)amino]-4,5-dihydro-1H-imidazol-5-one |

-continued

| Compound ID | Name |
|---|---|
| TJU-B031 | (4Z)-4-[(2H-1,3-benzodioxol-5-yl)methylidene]-2-[(pyridin-3-yl)amino]-4,5-dihydro-1H-imidazol-5-one |
| TJU-B033 | (4Z)-4-[(2H-1,3-benzodioxol-5-yl)methylidene]-2-(methylamino)-4,5-dihydro-1H-imidazol-5-one |
| TJU-B034 | (4Z)-2-amino-4-[(2H-1,3-benzodioxol-5-yl)methylidene]-4,5-dihydro-1H-imidazol-5-one |
| TJU-B036 | (4Z)-2-amino-4-[(3-methoxyphenyl)methylidene]-1-methyl-4,5-dihydro-1H-imidazol-5-one |
| TJU-B038 | (4Z)-4-[(2H-1,3-benzodioxol-5-yl)methylidene]-2-[(propan-2-yl)amino]-4,5-dihydro-1H-imidazol-5-one |
| TJU-B039 | (4Z)-4-[(2H-1,3-benzodioxol-5-yl)methylidene]-2-phenyl-4,5-dihydro-1H-imidazol-5-one |
| TJU-B040 | (4Z)-4-[(2H-1,3-benzodioxol-5-yl)methylidene]-2-(ethylamino)-4,5-dihydro-1H-imidazol-5-one |
| TJU-B043 | (4Z)-4-[(2H-1,3-benzodioxol-5-yl)methylidene]-2-(phenylamino)-4,5-dihydro-1H-imidazol-5-one |
| TJU-B045 | (4Z)-2-amino-1-methyl-4-(phenylmethylidene)-4,5-dihydro-1H-imidazol-5-one |
| TJU-B049 | (4Z)-2-amino-4-[(2,2-difluoro-2H-1,3-benzodioxol-5-yl)methylidene]-4,5-dihydro-1H-imidazol-5-one |
| TJU-B050 | (4Z)-2-amino-4-[(4-fluorophenyl)methylidene]-1-methyl-4,5-dihydro-1H-imidazol-5-one |
| TJU-B051 | (4Z)-4-[(7-methoxy-2H-1,3-benzodioxol-5-yl)methylidene]-2-(phenylamino)-4,5-dihydro-1H-imidazol-5-one |
| TJU-B052 | (4Z)-4-[(2H-1,3-benzodioxol-5-yl)methylidene]-2-[(cyclopropylmethyl)amino]-1-methyl-4,5-dihydro-1H-imidazol-5-one |
| TJU-B056 | (4Z)-2-amino-4-[(3-chlorophenyl)methylidene]-1-methyl-4,5-dihydro-1H-zimidaol-5-one |
| TJU-B057 | (4Z)-2-amino-4-[(2H-1,3-benzodioxol-5-yl)methylidene]-1-methyl-4,5-dihydro-1H-imidazol-5-one |
| TJU-B058 | 4-{[(4Z)-4-[(2H-1,3-benzodioxol-5-yl)methylidene]-5-oxo-4,5-dihydro-1H-imidazol-2-yl]amino } benzonitrile |
| TJU-B059 | (4Z)-4-[(2H-1,3-benzodioxol-5-yl)methylidene]-2-cyclopropyl-4,5-dihydro-1H-imidazol-5-one |
| TJU-B060 | (4Z)-4-[(2H-1,3-benzodioxol-5-yl)methylidene]-2-[(4-chlorophenyl)amino]-4,5-dihydro-1H-imidazol-5-one |
| TJU-B063 | (4Z)-4-[(2,2-difluoro-2H-1,3-benzodioxol-5-yl)methylidene]-2-phenyl-4,5-dihydro-1H-imidazol-5-one |
| TJU-B064 | (4Z)-2-amino-4-[(6-chloro-2H-1,3-benzodioxol-5-yl)methylidene]-4,5-dihydro-1H-imidazol-5-one |
| TJU-B065 | (4Z)-2-amino-4-[(7-methoxy-2H-1,3-benzodioxol-5-yl)methylidene]-4,5-dihydro-1H-imidazol-5-one |
| TJU-B066 | (4Z)-4-[(2,2-difluoro-2H-1,3-benzodioxol-5-yl)methylidene]-2-{[2-(morpholin-4-yl)ethyl]amino}-4,5-dihydro-1H-imidazol-5-one |
| TJU-B067 | (4Z)-2-amino-4-[(2-fluorophenyl)methylidene]-1-methyl-4,5-dihydro-1H-imidazol-5-one |
| TJU-B070 | (4Z)-2-amino-4-[(3,4-dimethoxyphenyl)methylidene]-1-methyl-4,5-dihydro-1H-imidazol-5-one |
| TJU-B085 | (4Z)-4-[(3,4-dimethoxyphenyl)methylidene]-2-(phenylamino)-4,5-dihydro-1H-imidazol-5-one |
| TJU-B088 | (4Z)-2-[(2H-1,3-benzodioxol-5-yl)amino]-4-[(2H-1,3-benzodioxol-5-yl) methylidene]-1-methyl-4,5-dihydro-1H-imidazol-5-one |
| TJU-B097 | (4Z)-4-[(2H-1,3-benzodioxol-5-yl)methylidene]-2-[(pyridin-2-yl)amino]-4,5-dihydro-1H-imidazol-5-one |
| TJU-B110 | (4Z)-4-[(2H-1,3-benzodioxol-5-yl)methylidene]-2-[(4-methylphenyl)amino]-4,5-dihydro-1H-imidazol-5-one |
| TJU-B253 | (4Z)-4-[(2H-1,3-benzodioxol-5-yl)methylidene]-2-(cyclohexylamino)-4,5-dihydro-1H-imidazol-5-one |
| TJU-B254 | (4Z)-4-[(2H-1,3-benzodioxol-5-yl)methylidene]-2-[(2-methoxyphenyl)amino]-4,5-dihydro-1H-imidazol-5-one |

* * * * *